(12) United States Patent
Gerber et al.

(10) Patent No.: US 8,204,597 B2
(45) Date of Patent: Jun. 19, 2012

(54) EVALUATING PATIENT INCONTINENCE

(75) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1015 days.

(21) Appl. No.: 11/755,546

(22) Filed: May 30, 2007

(65) Prior Publication Data
US 2008/0300449 A1 Dec. 4, 2008

(51) Int. Cl.
A61B 5/20 (2006.01)
(52) U.S. Cl. .......................................... 607/41; 607/40
(58) Field of Classification Search .............. 600/29–30; 607/40–41
See application file for complete search history.

(56) References Cited

U.S. PATENT DOCUMENTS

| 5,593,431 A | 1/1997 | Sheldon |
| 2003/0100930 A1 | 5/2003 | Cohen et al. |
| 2004/0015100 A1 | 1/2004 | Schmidt |
| 2005/0115561 A1 | 6/2005 | Stahmann et al. |
| 2005/0209511 A1* | 9/2005 | Heruth et al. ................ 600/301 |
| 2005/0209513 A1* | 9/2005 | Heruth et al. ................ 600/301 |
| 2005/0209644 A1 | 9/2005 | Heruth et al. |
| 2006/0020225 A1 | 1/2006 | Gerber et al. |
| 2006/0190047 A1 | 8/2006 | Gerber et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0200205 A1 | 9/2006 | Haller |
| 2007/0100388 A1 | 5/2007 | Gerber |
| 2007/0225616 A1 | 9/2007 | Brown et al. |
| 2007/0255176 A1 | 11/2007 | Rondoni et al. |

FOREIGN PATENT DOCUMENTS

| WO | 2006/091611 A1 | 8/2006 |
| WO | 2006/092007 A1 | 9/2006 |

OTHER PUBLICATIONS

Chartier-Kastler et al. "LUTS/BPH in clinical practice: the importance of nocturia and quality of sleep," Journal Compilation, 98, Supplement 2, 3-8, (2006).
U.S. Appl. No. 11/414,504 to Rondoni et al., entitled "Voiding Detection With Learning Mode," filed Apr. 28, 2006.
U.S. Appl. No. 11/414,508 to Rondoni et al., entitled "External Voiding Sensor System," filed Apr. 28, 2006.
U.S. Appl. No. 11/691,405 to Heruth et al., entitled "Detecting Sleep," filed Mar. 26, 2007.

(Continued)

Primary Examiner — Carl H Layno
Assistant Examiner — Jennifer Ghand
(74) Attorney, Agent, or Firm — Shumaker & Sieffert, P.A.

(57) ABSTRACT

Systems and methods for determining a number of interruptions in a sleep state of a patient attributable to an urge or need to void during a sleep event include monitoring an activity level of the patient. The urge or need to void may be attributable to fecal or urinary incontinence. The patient activity level may be determined with one or more sensors that detect motion and/or one or more sensors that monitor a physiological parameter of the patient that varies as a function of patient activity. In one embodiment, a clinician selects a therapy parameter set for the patient based on the severity of the patient's incontinence. In another embodiment, the number of interruptions in the sleep state is associated with a therapy parameter set that was implemented during the sleep state in order to evaluate the efficacy of the therapy parameter set.

27 Claims, 13 Drawing Sheets

OTHER PUBLICATIONS

U.S. Appl. No. 11/691,425 to Heruth et al., entitled "Collecting Activity and Sleep Quality Information Via a Medical Device," filed Mar. 26, 2007.

U.S. Appl. No. 11/755,587 to Gerber et al., entitled "Voiding Event Identification Based on Patient Input," filed May 30, 2007.

U.S. Appl. No. 11/755,553 to Gerber et al., entitled "Collecting Activity Data for Evaluation of Patient Incontinence," filed May 30, 2007.

Notification of Transmittal of the International Search Report and the Written Opinion of the International Searching Authority, or the Declaration dated Aug. 6, 2008 for corresponding PCT Application PCT/US2008/061506 (10 pgs.).

Reply to Written Opinion dated Mar. 26, 2009 for corresponding PCT Application PCT/US2008/061506 (9 pgs.).

Notification of Transmittal of the International Preliminary Report on Patentability for corresponding PCT Application No. PCT/US2008/061506, dated Aug. 26, 2009 (7 pgs.).

\* cited by examiner

US 8,204,597 B2

EVALUATING PATIENT INCONTINENCE

TECHNICAL FIELD

The invention relates to medical device systems, and more particularly, to medical device systems for evaluating incontinence.

BACKGROUND

Many people suffer from an inability to control urinary function, i.e., urinary incontinence. Different muscles, nerves, organs and conduits within the urinary tract cooperate to collect, store and release urine. A variety of disorders may compromise urinary tract performance and contribute to incontinence. Many of the disorders may be associated with aging, injury or illness. For example, aging can often result in weakened sphincter muscles, which cause incontinence, or weakened bladder muscles, which prevent complete emptying. Some patients also may suffer from nerve disorders that prevent proper triggering and operation of the bladder or sphincter muscles.

One symptom of urinary incontinence is nocturia, which is characterized by the need to urinate while a patient is sleeping (i.e., during a sleep event), thereby possibly interrupting a sleep state of the patient. Nocturia may also be a symptom of other problems, such as interstitial cystitis, diabetes, benign prostatic hyperplascia or prostate cancer.

Fecal incontinence is the inability to control bowel function. Fecal incontinence may be attributable to many physiological conditions, such as muscle damage to the muscles of the rectum (e.g., the anal internal or external sphincters), nerve damage, loss of storage capacity within the rectum, and pelvic floor dysfunction. One symptom of fecal incontinence is similar to nocturia in that a patient experiences a fecal voiding urge during a sleep event.

Electrical stimulation of nerves in the pelvic floor may provide an effective therapy for a variety of disorders, including urinary incontinence and fecal incontinence. For example, an implantable electrical stimulator may be provided. The electrical stimulator may be a neurostimulator that delivers electrical stimulation to the sacral nerve to induce sphincter constriction and thereby close or maintain closure of the urethra at the bladder neck. In addition, electrical stimulation of the bladder wall may enhance pelvic floor muscle tone and assist fluid retention in the bladder or voiding fluid from the bladder.

SUMMARY

In general, the invention is directed toward systems and methods for collecting activity data of a patient during a sleep event to evaluate the severity of a patient's urinary or fecal incontinence, and particularly, a urge or need to void during a sleep event or to evaluate the efficacy of one or more therapies or therapy parameter sets to treat the incontinence. The patient's urges to void during a sleep event may be attributable to, for example, urinary incontinence or fecal incontinence. The systems and methods of the invention include detecting a sleep state of the patient and determining a number of times the patient's sleep is interrupted during the sleep state to void by identifying the number of times the patient awakes and engages in activity that indicates the patient has gotten up to void (e.g., a number of "awake counts"). The "sleep state" is typically one sleep event, such as one night of sleep, where the sleep state does not necessarily mean that the patient is asleep, but may include the time in which the patient is attempting to sleep. Furthermore, reference to an "awake" state does not imply any particular level of consciousness, but rather that physical activity was undertaken by the patient to void.

In some embodiments, the number of interruptions of sleep may be used to evaluate the severity of the urge to void during a sleep event prior to selecting a therapy parameter set for the patient or prior to selecting a therapy for the patient. In other embodiments, monitoring a number of interruptions in the sleep state of the patient helps indicate whether a therapy or therapy parameter set implemented during the sleep state is effective. In other embodiments, a therapy parameter may be adjusted based on the number of interruptions in the sleep state of the patient.

A device, such as a medical device that delivers therapy to the patient to control the incontinence, a clinician programming device, a patient programming device or another computing device, may determine a number of awake counts by monitoring and analyzing a signal generated by a sensor, where the signal varies as a function of patient activity. For example, a sensor that detects motion, such as an accelerometer or a piezoelectric crystal, may generate the signal. In addition or instead of the motion detecting sensor, the patient activity data may be collected via a sensor that generates a signal that indicates a physiological parameter that varies as a function of patient activity. In some embodiments, a single sensor is used to monitor the activity level of the patient. In other embodiments, multiple sensors are used, where the sensors may be positioned at the same or different locations on the patient. The sensors may be external or implanted.

In one embodiment, an awake count is recorded each time the patient transitions from a sleep state to an awake state and then back to the sleep state. For example, an awake count may be recorded when the patient transitions from a relatively low activity level to a high activity level and back to the low activity level after the beginning of a sleep state, because such a pattern of activity indicates that the patient was sleeping or attempting to sleep, got up to void, and then went back to sleep or attempting to sleep. As another example, transitions between the sleep state and awake state may be determined based on one or more sleep metrics that indicate a probability that the patient is in the sleep state or in an awake state.

In one embodiment, the invention is directed to a method comprising detecting a sleep state of a patient afflicted with sleep event voiding, monitoring an activity level of the patient via an implanted medical device, and determining a number of interruptions in the sleep state of the patient based on the monitored activity level to evaluate the sleep event voiding.

In another embodiment, the invention is directed to a method comprising detecting a sleep state of a patient, monitoring an activity level of the patient via a medical device, determining a number of interruptions in the sleep state of the patient based on the monitored activity level, and adjusting a therapy parameter to control sleep event voiding based on the number of interruptions in the sleep state.

In another embodiment, the invention is directed to a system comprising an implantable activity sensor that generates a signal that varies as a function of activity of a patient, and at least one processor that receives the signal from the activity sensor, detects a sleep state of the patient, and determines a number of interruptions in the sleep state of the patient based on the signal, and determines a second number of sleep event voiding events based on the number of interruptions in the sleep state of the patient.

In another embodiment, the invention is directed to a system comprising an activity sensor that generates a signal that varies as a function of activity of a patient, a therapy delivery module configured to deliver a therapy to the patient to control sleep event voiding, and at least one processor. The at least one processor receives the signal from the activity sensor, detects a sleep state of the patient, determines a number of interruptions in the sleep state of the patient based on the signal, and adjusts a parameter of the therapy based on the number of interruptions in the sleep state.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
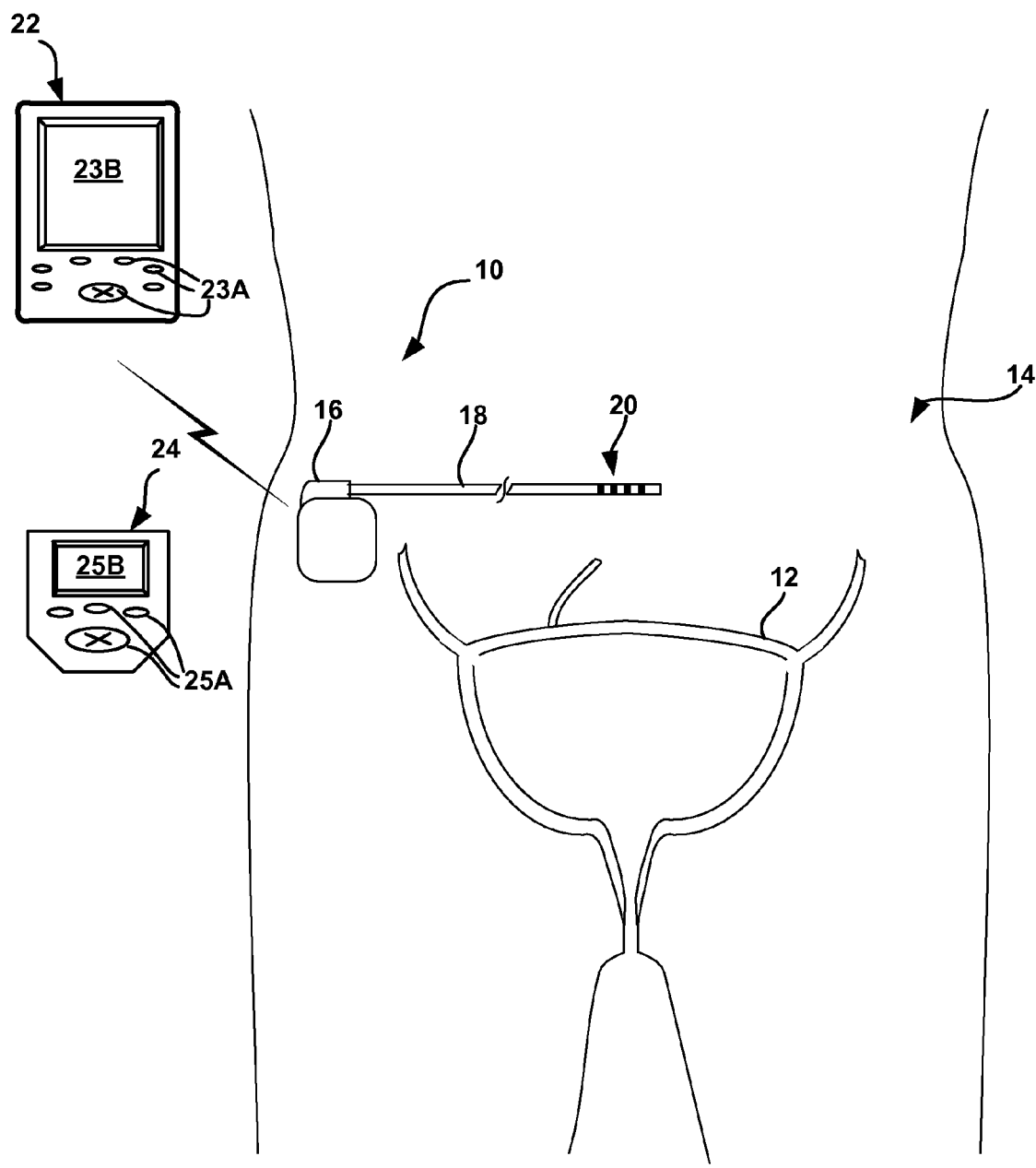
FIG. 1 is a schematic diagram illustrating a therapy system that provides electrical stimulation therapy to control the function of a bladder of a patient.

Urinary or fecal incontinence is a condition that affects the quality of life and health of many people. One symptom of urinary incontinence is nocturia, which may also be a symptom of other problems, such as interstitial cystitis, diabetes, benign prostatic hyperplascia or prostate cancer. Patients afflicted with fecal incontinence may also experience a symptom similar to nocturia, and in particular, a need or urge to void during a sleep event. In general, the urge or need to void during a sleep event may be referred to as "sleep event voiding." Sleep event voiding may disrupt a patient's sleep because of a reoccurring need or urge to void during a sleep state, which in turn may affect the patient's quality of life. The failure to get a full night of rest may adversely impact the patient's performance during the day, such as by causing fatigue or inattentiveness. While the remainder of the description primarily refers to nocturia, the present invention also applies to fecal incontinence and sleep event voiding attributable to fecal incontinence.

As an example, nocturia may be managed with electrical stimulation therapy that prevents urine from leaving the bladder when a patient does not wish to void urine. The electrical stimulation may be delivered to nerves, i.e., sacral or pudendal nerves, or directly to a urinary sphincter, where the stimulation causes the urinary sphincter to constrict and retain urine within the bladder. Electrical stimulation may also be directed to other muscles of the pelvic floor because some of these muscles play a role in controlling urinary voiding events. An electrical stimulator may be programmed to deliver electrical stimulation while the patient is sleeping in order to control the patient's nocturia. In some patients, nocturia accompanies other types of incontinence, such as urge incontinence, that may cause involuntary voiding events (e.g., involuntary leakage of urine) during the day. In such cases, the electrical stimulation may be provided to control the patient's bladder both during the day and at night. Different stimulation therapy parameter sets having different stimulation parameters (e.g., voltage or current amplitude, pulse width or pulse frequency of the stimulation) may be used to control the bladder during the day versus at night. Different parameter sets may be necessary because the bladder may be subject to different pressures during the day when the patient is typically upright and more active than while the patient is sleeping and typically recumbent.

An exemplary range of electrical stimulation parameters likely to be effective in treating urinary incontinence or fecal incontinence, e.g., when applied to a sacral (e.g., S3 sacral nerve) or pudendal nerves, are as follows:

1. Frequency: between approximately 0.5 Hertz (Hz) and approximately 500 Hz, such as between approximately 5 Hz and approximately 250 Hz or such as between approximately 10 Hz and approximately 50 Hz.
2. Amplitude: between approximately 0.1 volts and approximately 50 volts, such as between approximately 0.5 volts and approximately 20 volts or between approximately 1 volt and approximately 10 volts. The amplitude may be representative of a biological load between 10 ohms and approximately 10,000 ohms.
3. Pulse Width: between approximately 10 microseconds and approximately 5000 microseconds, such as between approximately 100 microseconds and approximately 1000 microseconds or between approximately 180 microseconds and 450 approximately microseconds.

Other electrical stimulation parameters may also be useful for managing urinary incontinence.

A patient may still be afflicted with nocturia despite receiving electrical stimulation therapy. The physiological characteristics of the patient may change and change the patient's response to stimulation parameters that once proved effective. In order to provide optimal therapy, the stimulation parameters may need to be modified periodically as the physiological characteristics of the patient changes. However, the clinician and/or patient may not always be aware of the changes. Systems and methods described herein are useful for collecting data related to the sleep quality of the patient to evaluate the efficacy of one or more therapy parameter sets to treat nocturia, regardless of whether the therapy parameter set includes electrical stimulation therapy, drug delivery therapy, a combination thereof or otherwise. Monitoring the number of interruptions in a sleep state of a patient helps indicate whether a therapy is effective and may also be used to rank the efficacy of multiple therapy parameter sets relative to each other. The interruptions in the patient's sleep state may generally indicate an event in which the patient is awoken by nocturia (i.e., because the patient must get out of bed to void).

The systems and methods described are also useful for evaluating the extent of the patient's nocturia by creating a log of the number of times the patient's sleep state is interrupted during a sleep event. The sleep event is generally measured between the commencement of a sleep state, such as when the patient begins attempting to sleep (i.e., a sleep initiation state), until the end of the sleep state, such as when the patient wakes up in the morning (although it need not necessarily be morning). As described in further detail below, the end of the sleep state is distinguishable from interruptions in the sleep state, after which the patient returns to the sleep state. Evaluating the extent of the patient's nocturia using the systems and methods described herein may be useful for diagnosing the severity of the patient's nocturia, such as to select a therapy parameter set for the patient. Furthermore, embodiments according to the invention need not include delivery of therapy or a therapy-delivering device.

FIG. 1 is a schematic diagram illustrating therapy system 10 that provides electrical stimulation therapy to control the function of bladder 12 of patient 14, such as to treat urinary incontinence. Electrical stimulation system 10 includes implantable medical device (IMD) 16, implantable medical lead 18, electrodes 20 disposed proximate to a distal end of lead 18, clinician programmer 22, and patient parameter programmer 24. IMD 16 at least partially prevents involuntary and unwanted urinary voiding events by providing stimulation to a pelvic floor nerve, a pelvic floor muscle or the urinary sphincter. In addition, as described in further detail below, IMD 16 collects information relating to the efficacy of the stimulation therapy provided by IMD 16. For example, IMD 16 may include, or may be coupled to, a sensor that detects an activity level of patient 14. Activity data from the sensor may be used to evaluate the efficacy of a stimulation parameter set implemented by IMD 16 to control the patient's nocturia. The activity data from the sensor may be provided to a user, such as a clinician, for evaluation, or alternatively, IMD 16 may evaluate the activity data and adjust the stimulation parameters based on the activity data.

IMD 16 provides a programmable stimulation signal (e.g., in the form of electrical pulses or substantially continuous-time signals) that is delivered to a target tissue site (e.g., the urinary sphincter, or sacral or pudendal nerves) by implantable medical lead 18, and more particularly, via one or more stimulation electrodes 20 carried by lead 18. In some embodiments, IMD 16 may be coupled to two or more leads, e.g., for bilateral or multi-lateral stimulation. A proximal end of lead 18 may be both electrically and mechanically coupled to IMD 16 either directly or indirectly (e.g., via a lead extension). Conductors disposed within a lead body of lead 18 electrically connect stimulation electrodes 20 (and sense electrodes, if present) to a therapy module within IMD 16.

Therapy system 10 may also include clinician programmer 22 and patient programmer 24. Clinician programmer 22 may be a handheld computing device that permits a clinician to communicate with IMD 16 during initial programming of IMD 16, and for collection of information and further programming during follow-up visits. Clinician programmer 22 supports telemetry (e.g., radio frequency (RF) telemetry or telemetry via the Medical Implant Communication Service (MICS) with IMD 16 to download electrical stimulation parameters to the IMD and, optionally, upload operational, patient activity data or other data stored, and some times collected, by IMD 16. In this manner, the clinician may periodically interrogate IMD 16 to evaluate efficacy of the stimulation therapy and, if necessary, modify the stimulation parameters.

Clinician programmer 22 may also include a user interface comprising keypad 23A and display 23B. A user, such as the clinician, may interact with clinician programmer 22 via keypad 23A and display 23B. For example, the clinician may parameter set stimulation therapy for patient 14, e.g., using input keys 23A and display 23B. Input keys 23A may take the form of an alphanumeric keypad or a reduced set of keys associated with particular functions. Display 23B may be an LCD or LED display. In some embodiments, display 23B may be a touch screen display, and a user may interact with clinician programmer 22 via display 23B. A user may also interact with clinician programmer 22 using a peripheral pointing device, such as a stylus or mouse.

Like clinician programmer 22, patient programmer 24 may be a handheld computing device. Patient programmer 24 may also include a user interface comprising input keys 25A and a display 25B to allow patient 14 to interact with patient programmer 24 and IMD 16. In this manner, patient programmer 24 provides patient 14 with an interface to control of stimulation therapy delivered by IMD 16. For example, patient 14 may use patient programmer 24 to start, stop or adjust neurostimulation therapy. In particular, patient programmer 24 may permit patient 14 to adjust stimulation parameters such as duration, amplitude, pulse width and pulse rate, within an adjustment range specified by the clinician via patient programmer 24, or select from a library of stored stimulation therapy parameter sets. Patient 14 may also retrieve information collected by IMD 16 via patient programmer 24. For example, patient programmer 24 may provide patient activity or nocturia data to patient 14 in the form of, for example, a statistic, a graphical representation, or a message relating to prevalence of nocturia or therapy efficacy.

Input keys 25A may take the form of an alphanumeric keypad or a reduced set of keys associated with particular functions. Display 25B may be an LCD or LED display. In some embodiments, display 25B may be a touch screen display, and a user may interact with patient programmer 24 via display 25B. A user may also interact with patient programmer 24 using a peripheral pointing device, such as a stylus or mouse.

IMD 16, clinician programmer 22, and patient programmer 24 may communicate via cables or a wireless communication, as shown in FIG. 1. Clinician programmer 22 and patient programmer 24 may, for example, communicate via wireless communication with electrical stimulator 16 using RF telemetry techniques known in the art. Clinician programmer 22 and patient programmer 24 also may communicate with each other using any of a variety of local wireless communication techniques, such as RF communication according to the 802.11 or Bluetooth specification sets, infrared communication, e.g., according to the IrDA standard, or other standard or proprietary telemetry protocols. In some embodiments, programmers 22, 24 may communicate via a wired connection, such as via a serial communication cable, or via exchange of removable media, such as magnetic or optical disks, or memory cards or sticks. Further, clinician programmer 22 may communicate with one or both of IMD 16 and patient programmer 24 via remote telemetry techniques known in the art, communicating via a local area network (LAN), wide area network (WAN), public switched telephone network (PSTN), or cellular telephone network, for example.

Clinician and patient programmers 22, 24 are not limited to the hand-held computer embodiments illustrated in FIG. 1. Programmers 22, 24 according to the invention may be any sort of computing device. For example, a programmer 22, 24 according to the invention may be a tablet-based computing device, a desktop computing device, or a workstation.

As mentioned above, IMD 16 collects information that relates to the activity of the patient 14 in order to determine a number of interruptions in a sleep state of patient 14. In particular, as will be described in greater detail below, IMD 16 monitors an activity level of patient 14 in order to determine when patient 14 transitions from a sleep state to an awake state and back to the sleep state, which thereby indicates that the patient has awoken to void, and then returned to bed rather than ending the sleep state. An "awake" state does not imply any particular level of consciousness, but rather that physical activity was undertaken by the patient to void. The transitions between the sleep state and awake state are used to determine whether the patient's sleep is interrupted because of nocturia. Typically, the relevant determination is whether the patient's sleep is interrupted because of a need or desire to get out of bed to void. Thus, the "awake state" refers to a state in which patient 14 is not only not asleep, but is active. The activity level is selected to reflect a patient activity level that occurs when patient 14 moves from, e.g., a bed to a bathroom to void or gets out of bed. While the interruption in the sleep state may be attributable to other reason, such as to answer a telephone call, the activity level is used in the present invention as a general indicator of interruptions in the sleep state, which generally represent interruptions due to nocturia.

At any given time, IMD 16 delivers electrical stimulation therapy according to a current set of therapy parameters. Different therapy parameter sets may be selected, e.g., by a patient 14 via patient programmer 24 or IMD 16 according to a schedule, and parameters of one or more therapy parameter sets may be adjusted by a patient 14 via patient programmer 24 to create new therapy parameter sets. In other words, over time, IMD 16 delivers the therapy according to a plurality of therapy parameter sets.

In some embodiments, as will be described in greater detail below, IMD 16 identifies the therapy parameter set currently used to deliver therapy to a patient 14, and associates any interruptions to a sleep state that occur when the therapy parameter set is used with the therapy parameter set. Based on the interruptions associated with various parameter sets, IMD 16 may facilitate an evaluation of, or itself determine, a total number of interruptions (hereinafter referred to as "awake counts") during a single sleep state or an average of interruptions over a period of time, such as a week. For each of the plurality of therapy parameter sets, IMD 16 may store a representative value of the respective number of awake counts in a memory with an indication of the therapy parameter set with which the representative number of awake counts is associated. A representative number of awake counts for a therapy parameter set may be the mean or median of collected awake counts that have been associated with that therapy parameter set. For each available therapy parameter set, IMD 16 may also store activity data associated with that therapy parameter set. The awake count associated with the therapy parameter set may be used to evaluate the efficacy of the therapy parameter set, as well as to determine what minimum level of therapy controls the patient's sleep event voiding. Determining the minimum level of energy may help conserve the energy consumed by IMD 16, and thus, increase the useful life of IMD 16.

A programmer or other computing device, such as clinician programmer 22, may receive information identifying the therapy parameter set and associated number of awake counts associated with the therapy parameter sets from IMD 16. Clinician programmer 22 may display a list of the therapy parameter sets, which may be ordered according to the associated number of awake counts. Such a list may be used by the clinician to, for example, identify effective or ineffective therapy parameter sets.

In some embodiments, the awake count information may also be used to determine whether it would be useful to turn IMD 16 off during a sleep event. For example, if the awake count information indicates that patient 14 does not experience any sleep event voiding events, IMD 16 may be turned off during a sleep event in order to conserve energy. Conserving energy may help increase the longevity of the useful life of IMD 16 may extending the life of the power source within IMD 16. IMD 16 may be set on, for example, a timer that regularly turns off the IMD or reverts the IMD to a sleep mode during a patient's sleep event (e.g., at night). Alternatively, patient 14 may manually turn IMD 16 on and off via patient programmer 24 prior to a sleep event.

Figure 2:
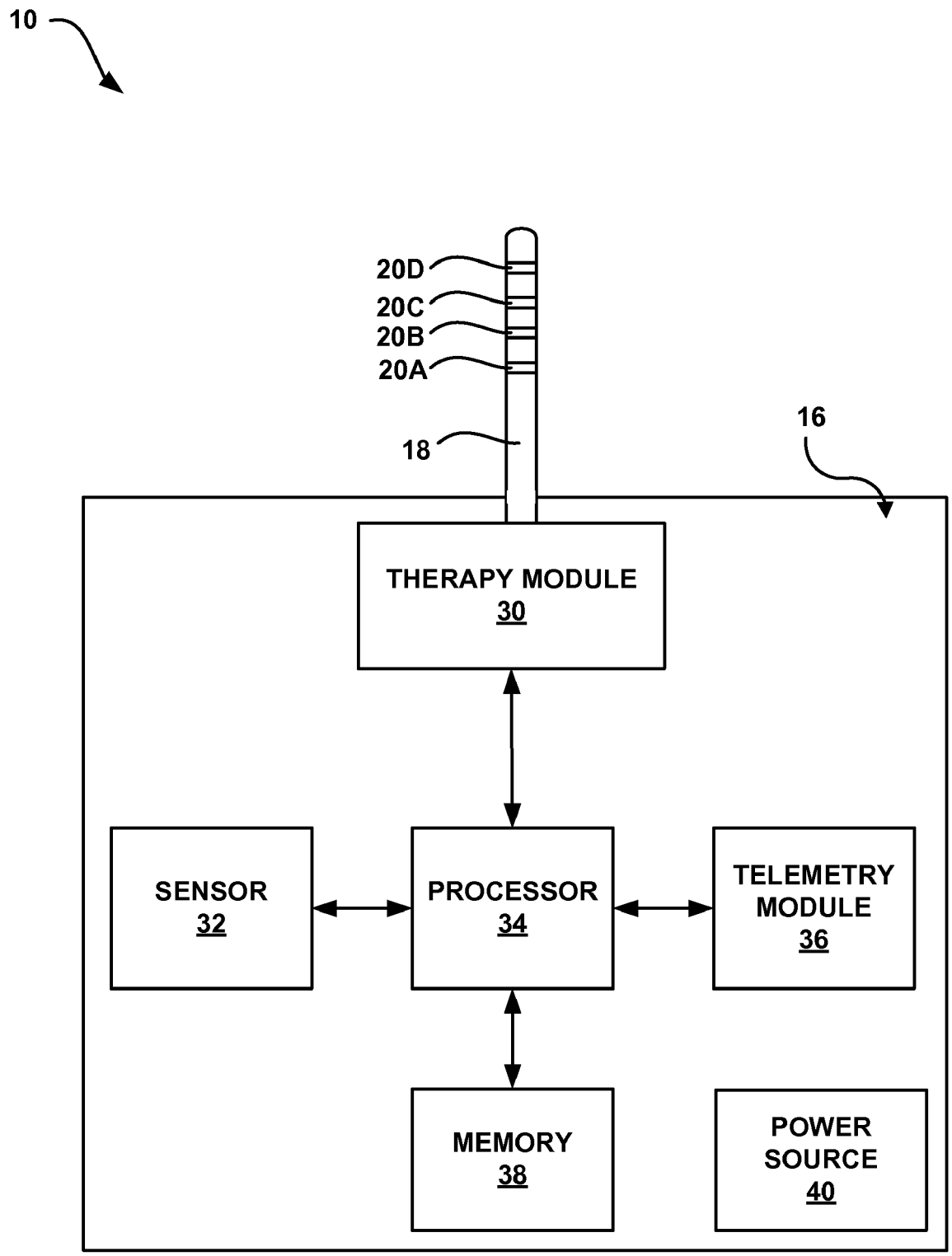
FIG. 2 is a block diagram illustrating various components of one embodiment of an implantable medical device and implantable medical lead.

FIG. 2 is a block diagram illustrating various components of one embodiment of IMD 16 and implantable medical lead 18. IMD 16 is configured to deliver electrical stimulation therapy to target nerves or other tissue sites within or proximate to bladder 12 via electrodes 20A-D of lead 18 to control the function of bladder 12. In particular, IMD 16 minimizes unwanted urinary voiding events by delivering electrical stimulation to, e.g., a pelvic floor nerve, a pelvic floor muscle or the urinary sphincter.

IMD 16 includes therapy module 30, sensor 32, processor 34, telemetry module 36, memory 38, and power source 40. In the embodiment shown in FIG. 2, implantable medical lead 18 is cylindrical. In other embodiments, implantable medical lead 18 may be, at least in part, paddle-shaped (i.e., a "paddle" lead). In some embodiments, electrodes 20A-D (collectively "electrodes 20") may be ring electrodes. In other embodiments, electrodes 20 may be segmented or partial ring electrodes, each of which extends along an arc less than 360 degrees (e.g., 90-120 degrees) around the outer perimeter of lead 18. The configuration, type, and number of electrodes 20 illustrated in FIG. 2 are merely exemplary.

Electrodes 20 are electrically coupled to a therapy module 30 of IMD 16 via conductors within lead 18. In one embodiment, an implantable signal generator or other stimulation circuitry within therapy module 30 delivers electrical signals (e.g., pulses or substantially continuous-time signals, such as sinusoidal signals) to bladder 12 (FIG. 1) via at least some of electrodes 20 under the control of processor 34. The stimulation energy generated by therapy module 30 may delivered from therapy module 30 to selected electrodes 20 via a switch matrix and conductors carried by lead 18, as controlled by processor 34.

Processor 34 may include any one or more of a microprocessor, a controller, a digital signal processor (DSP), an application specific integrated circuit (ASIC), a field programmable gate array (FPGA), discrete logic circuitry, or the like. Processor 34 controls the implantable signal generator within therapy module 30 to deliver electrical stimulation therapy according to selected stimulation parameters. Specifically, processor 34 controls therapy module 30 to deliver electrical signals with selected voltage or current amplitudes, pulse widths (if applicable), and rates specified by the stimulation parameters (i.e., therapy parameter sets). In addition, processor 34 may also control therapy module 30 to deliver the electrical stimulation signals via selected subsets of electrodes 20 with selected polarities. For example, electrodes 20 may be combined in various bipolar or multi-polar combinations to deliver stimulation energy to selected sites, such as nerve sites adjacent the spinal column, pelvic floor nerve sites, or cranial nerve sites. The above-mentioned switch matrix may be controlled by processor 34 to configure electrodes 20 in accordance with a therapy parameter set.

Processor 34 may also control therapy module 30 to deliver each stimulation signal according to a different parameter set, thereby interleaving parameter sets to simultaneously treat different symptoms or provide a combined therapeutic effect. For example, in addition to treatment incontinence, IMD 16 may also be configured to deliver electrical stimulation therapy to treat other symptoms such as pain or sexual dysfunction.

Memory 38 of IMD 16 may include any volatile or nonvolatile media, such as any one or more of a random access memory (RAM), read-only memory (ROM), non-volatile RAM (NVRAM), electronically-erasable programmable ROM (EEPROM), flash memory, and the like. In some embodiments, memory 38 may store multiple therapy parameter sets that are available to be selected by patient 14 via patient programmer 24 (FIG. 1) or a clinician via clinician programmer 22 (FIG. 1) for delivery of stimulation therapy. For example, memory 38 may store stimulation parameters transmitted to IMD 16 by clinician programmer 22 (FIG. 1). Memory 38 also stores parameter set instructions that, when executed by processor 34, cause therapy module 30 to deliver electrical stimulation to target tissue site, such as muscles or nerves of bladder 12, record activity information, and determine activity counts. Accordingly, computer-readable media storing instructions may be provided to cause processor 34 to provide functionality as described herein.

Memory 38 may also store data generated by sensor 32 and/or processor 34. In one embodiment, memory 38 implements loop recorder functionality in which processor 34 overwrites the oldest contents within memory 38 with new data as storage limits are met, thereby conserving data storage resources. Because the capacity of memory 38 is limited, in order to record large amounts of data and/or record data over a relatively long period of time, it may be useful to record the patient activity data from sensor 32 with a loop recorder.

Processor 34 may also control telemetry module 36 to exchange information with an external programmer, such as clinician programmer 22 and/or patient programmer 24 (FIG. 1), by wireless telemetry. In addition, in some embodiments, telemetry module 36 supports wireless communication with one or more wireless sensors that generate signals indicative of physiological parameters or motion of patient 14 and transmit the signals to IMD 16. Such communication may be via any wireless communication protocol, such as known medical device telemetry protocols, or the Bluetooth protocol.

Therapy module 30 and processor 34 may be coupled to power source 40. Power source 40 may take the form of a small, rechargeable or non-rechargeable battery, or an inductive power interface that transcutaneously receives inductively coupled energy. In the case of a rechargeable battery, power source 40 similarly may include an inductive power interface for transcutaneous transfer of recharge power.

Sensor 32 is configured to generate a signal indicative of a patient activity level. As will be described in greater detail below, processor 34 monitors a signal from sensor 32 to determine how many times patient 14 transitions between a sleep state and an awake and active state during a sleep event, which is representative of the interruptions in sleep attributable to nocturia.

Sensor 32 may be any sensor such as an accelerometer (e.g., one or more multiple axis accelerometers or one or more single axis accelerometers arranged along one or more axes), a bonded piezoelectric crystal, a mercury switch, or a gyro, or any other sensor that transforms mechanical, chemical or electrical conditions into electrical signals representative of an activity level of patient 14. A multiple axis accelerometer, also referred to as a multi-axis accelerometer, or multiple single axis accelerometers may be useful for generating a signal that may be used to determine both a patient activity level and a patient posture. The electrical signals from sensor 32 may be amplified, filtered, and otherwise processed as appropriate by circuitry known in the art, which may be provided as part of sensor 32 or processor 34. In some embodiments, the signals may be converted to digital values and processed by processor 34 before being saved to memory 38 or uploaded to another device (e.g., clinician programmer 22 or patient programmer 24).

In some cases, an IMD may include a sensor that generates a signal that is indicative of a physiological parameter measurement of patient 14 that varies as a function of patient activity. The relevant physiological parameters include, but are not limited to, heart rate, respiratory rate, electrocardiogram (ECG) morphology, respiration rate, respiratory volume, core temperature, a muscular activity level or subcutaneous temperature of the patient. The physiological sensor may be used in addition to or instead of sensor 32 that generates a signal indicative of patient motion.

Figure 3:
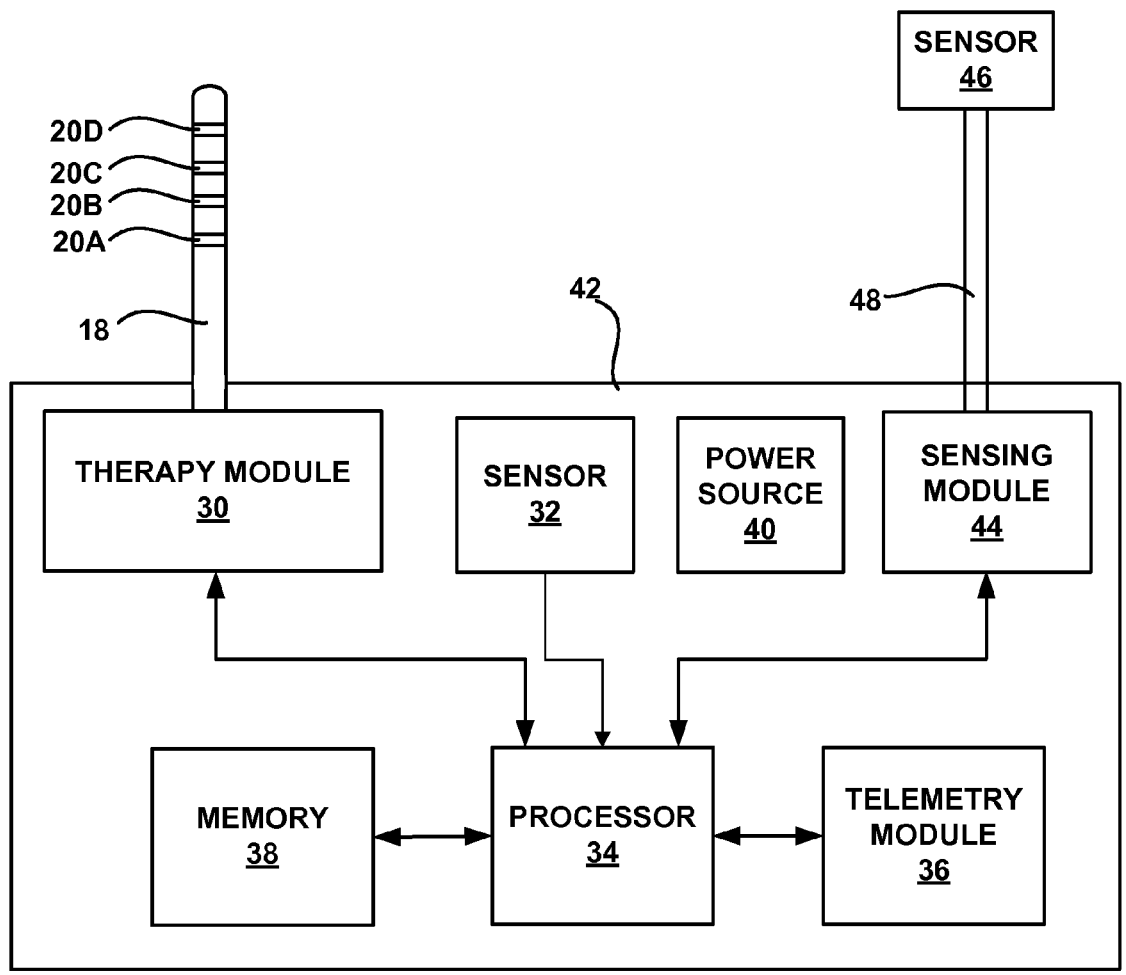
FIG. 3 is a block diagram of another embodiment of an implantable medical device, which includes a physiological parameter sensor.

FIG. 3 is a schematic block diagram of another embodiment of IMD 42, which is similar to IMD 16, but includes physiological parameter sensing module 44 that is electrically coupled to physiological parameter sensor 46 via implantable lead 48. As described in further detail below, processor 34 monitors at least some of the signals from physiological parameter sensor 46 to estimate the number of interruptions in a sleep state of patient 14 that are attributable to nocturia. Processor 34 may monitor signals from sensor 32 in addition to signals from sensor 46. In some embodiments, IMD 42 may not include sensor 32 that generates a signal indicative of patient motion, but may instead rely on signals from sensor 46 to determine when patient 14 transitions between a sleep state and an awake state in order to estimate the number of interruptions in a sleep state of patient 14 that are attributable to nocturia.

Sensing module 44 includes the sensing circuitry, and may generate a signal indicative of one or more physiological parameters sensed by sensor 46 and transmit the signal to processor 34. Sensing module 44, or alternatively, processor 34, may include circuitry that conditions the signals generated by sensor 46 such that they may be analyzed by processor 34. For example, sensing module 44 may include one or more analog to digital converters to convert analog signals generated by sensors 46 into digital signals usable by processor 34, as well as suitable filter and amplifier circuitry. Although shown as including a single sensor 46, any number of sensors may be coupled to IMD 42.

Sensor 46 may include one or more electrodes located on lead 48 or more than one lead. Alternatively, one or more physiological parameter sensors (e.g., one or more sensing electrodes) may be disposed on a housing of IMD 42. In another embodiment, one or more physiological sensors may be coupled to IMD 42 via wireless telemetry supported by telemetry module 36 or another telemetry module configured to communicate with the wireless sensor. Exemplary physiological parameters of patient 14 that may be monitored by sensor 46 include activity, posture, heart rate, ECG morphology, respiration rate, respiratory volume, blood pressure, blood oxygen saturation, partial pressure of oxygen within blood, partial pressure of oxygen within cerebrospinal fluid (CSF), muscular activity and tone, core temperature, subcutaneous temperature, arterial blood flow, the level of melatonin within one or more bodily fluids or brain electrical activity. Further, in some external medical device embodiments of the invention, galvanic skin response may additionally or alternatively be monitored. Sensor 46 may be of any type known in the art capable of generating a signal as a function of one or more of these parameters.

In one embodiment, sensor 46 detects an electrogram signal and sensing module 44 generates an electrogram signal as a function of electrical activity of the heart of patient 14. Processor 34 periodically determines the heart rate of patient 14 based on the electrogram signal. In other embodiments, sensor 46 may include an acoustic sensor, a pressure sensor within the bloodstream or cerebrospinal fluid of patient 14, or a temperature sensor located within tissue or the bloodstream of patient 14. The signals generated by such a sensor 46 may vary as a function of contraction of the heart of patient 14, and can be used by processor 34 to periodically determine the heart rate of patient 14, which may indicate an activity level of patient 14. As described in further detail below, the patient activity level may be monitored to determine whether patient 14 is in a sleep state or an awake state.

In some embodiments, processor 34 may detect, and measure values for one or more ECG morphological features within an electrogram generated by electrodes as described above. ECG morphological features may vary in a manner that indicates whether a patient 14 is asleep or awake. For example, the amplitude of the ST segment of the ECG may decrease when patient 14 is asleep. Further, the amplitude of QRS complex or T-wave may decrease, and the widths of the QRS complex and T-wave may increase when a patient 14 is asleep. The QT interval and the latency of an evoked response may increase when a patient 14 is asleep, and the amplitude of the evoked response may decrease when the patient 14 is asleep.

In some embodiments, sensor 46 may include an electrode pair, including one electrode integrated with the housing of IMD 42, which generates a signal as a function of the thoracic impedance of patient 14, which varies as a function of respiration by patient 14. In other embodiments, sensor 46 may include a strain gauge, bonded piezoelectric element, or pressure sensor within the blood or cerebrospinal fluid that generates a signal that varies based on patient respiration. Processor 34 may monitor the signals generated by such a sensor 46 to periodically determine a respiration rate and/or respiratory volume of patient 14. An electrogram generated by electrodes as discussed above may also be modulated by patient respiration, and processor 34 may use the electrogram as an indirect representation of respiration rate.

Sensor 46 may also include electrodes that generate an electromyogram (EMG) signal as a function of muscle electrical activity, as described above, or may include any of a variety of known temperature sensors to generate a signal as a function of a core or subcutaneous temperature of a patient 14. Such electrodes and temperature sensors may be incorporated within the housing of IMD 42, or coupled to IMD 42 wirelessly or via one or more leads 48. Sensor 46 may also include a pressure sensor within, or in contact with, a blood vessel. The pressure sensor may generate a signal as a function of the a blood pressure of a patient 14, and may, for example, comprise a Chronicle Hemodynamic Monitor™ commercially available from Medtronic, Inc. of Minneapolis, Minn. Further, certain muscles of patient 14, such as the muscles of the patient's neck, may discernibly relax when the patient 14 is asleep or within certain sleep states. Consequently, sensor 46 may include one or more strain gauges or EMG electrodes implanted in such locations that generate a signal as a function of muscle tone and are wirelessly coupled to sensing module 44.

Sensor 46 may also include one or more optical pulse oximetry sensors or Clark dissolved oxygen sensors located within, as part of a housing of, or outside of IMD 42, which generate signals as a function of blood oxygen saturation and blood oxygen partial pressure respectively. In some embodiments, a therapy system may include a catheter with a distal portion located within the cerebrospinal fluid of patient 14, and the distal end may include a Clark dissolved oxygen sensor to generate a signal as a function of the partial pressure of oxygen within the cerebrospinal fluid. Embodiments in which an IMD comprises an implantable pump, for example, may include a catheter with a distal portion located in the cerebrospinal fluid.

In some embodiments, sensor 46 may include one or more intraluminal, extraluminal, or external flow sensors positioned to generate a signal as a function of arterial blood flow. A flow sensor may be, for example, an electromagnetic, thermal convection, ultrasonic-Doppler, or laser-Doppler flow sensor. Further, in some external medical device embodiments of the invention, sensor 46 may include one or more electrodes positioned on the skin of patient 14 to generate a signal as a function of galvanic skin response. Additionally, in some embodiments, sensor 46 may include one or more electrodes positioned within or proximate to the brain of patient, which detect electrical activity of the brain. In each of those embodiments, sensor 46 may be wirelessly coupled to sensing module 44.

Figure 4:
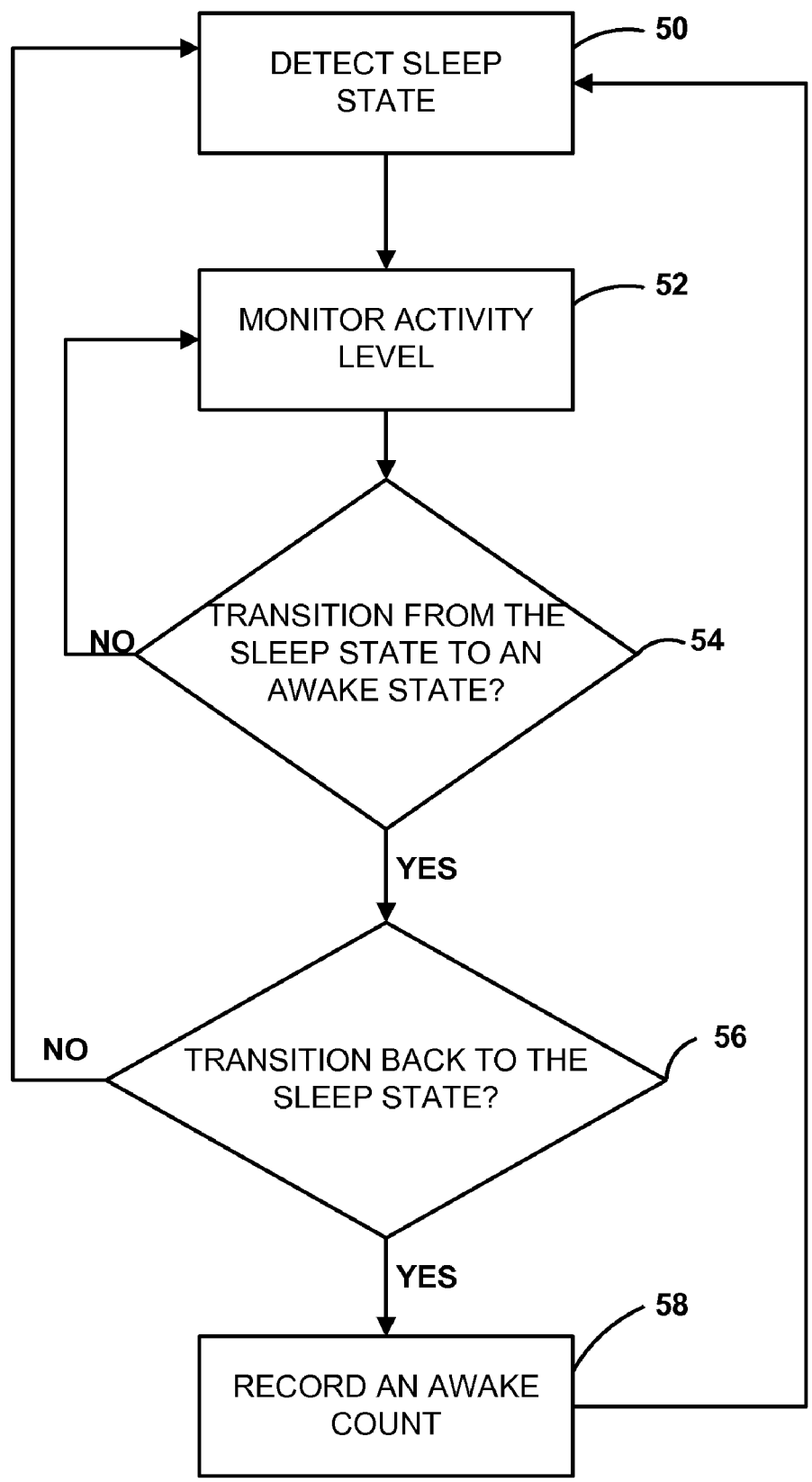
FIG. 4 is a flow diagram illustrating an embodiment of a method of determining a number of interruptions in a sleep state of patient based on feedback from sensors that generate a signal that varies as a function of patient activity.

FIG. 4 is a flow diagram illustrating a method of determining a number of interruptions in a sleep state of patient 14 based on feedback from motion sensor 32 and/or physiological parameter sensor 46. While IMD 42 is referred to throughout the description of FIG. 4, it should be understood that the description similarly applies to IMD 16 or other external or implantable medical devices including a sensor that generates a signal indicative of patient activity level. IMD 42 detects a sleep state of patient 14 is (50). A "sleep state" includes both a phase when patient 14 is attempting to sleep and when patient 14 is asleep. Because nocturia may disrupt the patient's rest by causing patient 14 to get up to urinate when patient 14 is attempting to sleep, counting the number of interruptions while patient 14 is attempting to sleep may be just as important in evaluating the efficacy of a therapy parameter set or the severity of the nocturia as the number of interruptions when patient 14 is asleep.

Processor 34 may identify when patient 14 is attempting to sleep in a variety of ways. For example, processor 34 may identify the time that patient begins attempting to fall asleep based on an indication received from a patient 14. For example, patient 14 may provide an input via input keys 25A or display 25B of patient programmer 24, which may then be transmitted to IMD 42 and received via telemetry module 36. In another embodiment, patient 14 taps the general implant site of IMD 42 to indicate that the patient is attempting to sleep. As described in commonly-assigned U.S. patent application Ser. No. 11/755,587, entitled, "VOIDING EVENT IDENTIFICATION BASED ON PATIENT INPUT" to Martin T. Gerber, filed on May 30, 2007, which published on Dec. 4, 2008 as U.S. Publication No. 2008/0300651 and which is incorporated herein by reference in its entirety, tapping IMD 42 a certain amount of times or in a certain pattern may cause processor 34 within IMD 42 to record the date and time of the tapping or activate a feature of IMD 42.

In other embodiments, processor 34 detects the sleep state (50) by identifying the time that a patient 14 begins attempting to fall asleep based on the activity level of patient 14, which is monitored one or both sensors 32 and/or 46. A relatively low level of activity indicates that patient 14 has likely entered a sleep state. The low level of activity may be cross-checked with the time of day (i.e., if IMD 42 includes a clock) or the posture of patient 14 in order to confirm that patient 14 is entering a sleep state and not merely inactive. Techniques for determining the posture of patient 14 is described in detail below.

One technique processor 34 may employ to detect a sleep state is to identify a time when the activity level of a patient 14 falls below a threshold activity level value stored in memory 38 and determine whether the activity level remains substantially below the threshold activity level value for a threshold amount of time stored in memory 38. In other words, a patient 14 remaining inactive for a sufficient period of time may indicate that patient 14 is attempting to fall asleep, or has fallen asleep. If processor 34 determines that the threshold amount of time is exceeded, processor 34 may identify the time at which the activity level fell below the threshold activity level value as the time that the sleep state of patient 14 begins.

In some embodiments, sensor 46 may include one or more electrodes that generate an EMG signal as a function of muscle electrical activity, which may indicate the activity level of a patient. The electrodes may be, for example, located in the legs, abdomen, chest, back or buttocks of a patient 14 to detect muscle activity associated with walking, running or the like. The electrodes may be coupled to IMD 42 wirelessly or by lead 48 or, if IMD 42 is implanted in these locations, integrated with a housing of IMD 42. When processor 34 determines that the muscle electrically activity falls below a threshold, processor 34 may determine that patient 14 has entered a sleep state.

Bonded piezoelectric crystals located in the legs, abdomen, chest, back or buttocks of a patient 14 generate signals as a function of muscle contraction in addition to body motion, footfalls or other impact events. Consequently, use of bonded piezoelectric crystals to detect activity of a patient 14 may be preferred in some embodiments in which it is desired to detect muscle activity in addition to body motion, footfalls or other impact events. Thus, in one embodiment, sensor 46 includes one or more bonded piezoelectric crystals that are coupled to IMD 42 wirelessly or via a lead 48, or piezoelectric crystals may be bonded to the housing of IMD 42 if IMD 42 is implanted in these areas, e.g., in the back, chest, buttocks or abdomen of patient 14. If IMD 42 is used to deliver stimulation therapy to control the function of bladder 12 (FIG. 1), however, IMD 42 may be implanted proximate to bladder 12, rather than in the back, chest, buttocks or abdomen of patient 14.

In some embodiments, processor 34 determines whether patient 14 is attempting to fall asleep based on the posture of patient 14, i.e., whether patient 14 is or is not recumbent. In such embodiments, sensor 32 may include a plurality of accelerometers (e.g., one, two or three axis accelerometers), gyros, or magnetometers oriented orthogonally that generate signals which indicate the posture of a patient 14. In addition to being oriented orthogonally with respect to each other, each sensor 32 that is used (if multiple sensors are used) to detect the posture of a patient 14 may be generally aligned with an axis of the body of the patient 14. In one embodiment, sensor 32 comprises three orthogonally oriented posture sensors.

When sensor 32 includes one or more accelerometers, for example, that are aligned in this manner, processor 34 may monitor the magnitude and polarity of DC components of the signals generated by the accelerometers to determine the orientation of patient 14 relative to the Earth's gravity, e.g., the posture of patient 14. In particular, processor 34 may compare the DC components of the signals to respective threshold values stored in memory 38 of IMD 42 to determine whether patient 14 is or is not recumbent. Further information regarding use of orthogonally aligned accelerometers to determine patient posture may be found in a commonly assigned U.S. Pat. No. 5,593,431, which issued to Todd J. Sheldon.

Other motion detection sensors 32 that may generate a signal that indicates the posture of patient 14 include bonded piezoelectric crystals that generate a signal as a function of contraction of muscles. Physiological parameter sensors 46 generate a signal that indicates the posture of patient 14 include electrodes that generate an electromyogram (EMG) signal. Such sensors 32, 40 may be implanted in the legs, buttocks, abdomen, or back of patient 14, as described above, and communicate with processor 34 of IMD 42 via wireless telemetry or via a lead 48. The signals generated by such sensors when implanted in these locations may vary based on the posture of patient 14, e.g., may vary based on whether the patient is standing, sitting, or lying down.

Further, the posture of patient 14 may affect the thoracic impedance of the patient. Consequently, sensor 46 may include an electrode that is used in with an electrode integrated with the housing of IMD 42, where sensor 46 and/or the electrode on the housing of IMD 42 generates a signal as a function of the thoracic impedance of patient 14. Processor 34 may detect the posture or posture changes of patient 14 based on the signal that is indicative of the thoracic impedance. In one embodiment, electrodes that are wirelessly coupled to processor 34 may be located on opposite sides of the patient's thorax.

Additionally, changes of the posture of patient 14 may cause pressure changes with the cerebrospinal fluid of the patient. Consequently, sensor 46 may include pressure sensors coupled to one or more intrathecal or intracerebroventricular catheters, or pressure sensors coupled to IMD 42 wirelessly or via lead 48. CSF pressure changes associated with posture changes may be particularly evident within the brain of the patient, e.g., may be particularly apparent in an intracranial pressure (ICP) waveform.

In some embodiments, processor 34 considers both the posture and the activity level of patient 14 when determining whether patient 14 is attempting to fall asleep, and thus, the beginning of the sleep state. For example, processor 34 may determine whether a patient 14 is sleeping based on a sufficiently long period of sub-threshold activity, as described above, and may identify the time that patient began attempting to fall asleep as the time when patient 14 became recumbent prior to the determination that the patient is sleeping. Any of a variety of combinations or variations of these techniques may be used to determine to detect the sleep state, and a specific one or more techniques may be selected based on the sleeping and activity habits of a particular patient.

In other embodiments, processor 34 detects the sleep state (50) by determining when patient 14 is attempting to fall asleep based on the level of melatonin in a bodily fluid. In such embodiments, sensor 46 may take the form of a chemical sensor that is sensitive to the level of melatonin or a metabolite of melatonin in the bodily fluid, and estimate the time that patient 14 will attempt to fall asleep based on the detection. For example, processor 34 may compare the melatonin level or rate of change in the melatonin level to a threshold level stored in memory 38, and identify the time that threshold value is exceeded. Processor 34 may identify the beginning of the sleep state as the time that the melatonin level exceeds the threshold, or some amount of time after the threshold is exceeded. Any of a variety of combinations or variations of the above-described techniques may be used to determine detect the sleep state (50), and a specific one or more techniques may be selected based on the sleeping and activity habits of a particular patient.

When IMD 42 detects the sleep state (50), such as by receiving input from patient 14 or determining that patient 14 is attempting to sleep, IMD 42 monitors the activity level of patient (52) in order to detect whether the patient's sleep state is interrupted, and in particular, whether patient 14 gets up at any time during the sleep state to void. In one embodiment, IMD 42 monitors the patient activity level by monitoring a signal generated by motion sensor 32. In addition or instead of monitoring a signal from motion sensor 32, IMD 42 may monitor a patient activity level by monitoring one or more physiological parameters of patient 14 that vary as a function of patient activity, such as heart rate, electrocardiogram (ECG) morphology, respiration rate, respiratory volume, core temperature, subcutaneous temperature or muscle activity. Physiological parameter sensor 46 may be used to monitor the one or more physiological parameters. Combinations of signals from motion sensor 32 and physiological parameter sensor 46 may also be used to monitor the patient activity level.

Processor 34 of IMD 42 may determine a patient activity level based on the signal from sensor 32 and/or 46. In one embodiment, processor 34 determines a patient activity level by sampling the signal and determining a number of activity counts during the sample period. In one embodiment, processor 34 compares the signal generated by sensor 32 and/or 46 to one or more amplitude thresholds stored within memory 38. Processor 34 may identify each threshold crossing as an activity count. Where processor 34 compares the sample to multiple thresholds with varying amplitudes, processor 34 may identify crossing of higher amplitude thresholds as multiple activity counts. Using multiple thresholds to identify activity counts, processor 34 may be able to more accurately determine the extent of patient activity. In embodiments in which motion sensor 32 takes the form of a mercury switch, processor 34 may identify the number of switch contacts indicated during the sample period as the number of activity counts. Processor 34 may store the determined number of activity counts in memory 38 as an activity level in addition to or instead of storing the signals generated by sensor 32 and/or 46.

In embodiments in which sensor 46 generates a signal indicative of a physiological parameter of a patient, processor 34 may monitor a signal from sensor 46 and determine a physiological parameter measurement based on the signal. The physiological parameter measurement may be mean or median values of the physiological parameter over a certain period of time. Based on the physiological parameter values, processor 34 may determine an activity level by comparing the determined physiological parameter measurement to one or more thresholds stored within memory 38. A first threshold may indicate a first activity level, a second a threshold may indicate a second activity level that is greater than the first activity level, and so forth for as many activity levels as desired. Processor 34 may compare the measured physiological parameter to the thresholds to determine the activity level corresponding to the measured physiological parameter. For example, if the measured parameter exceeds the second threshold, but not a third threshold, the measured parameter falls within the second activity level.

If one or more physiological parameters are measured to determine a patient activity level, the physiological parameter measurements that represent different activity levels may differ between patients, depending on the type of physiological parameter. For example, patients that are physically fit may have a different heart rate at an elevated activity state than patients that are not physically fit. Thus, between those two groups of patients, using the same heart rate threshold for both patients as an indicator of activity level may not be entirely accurate. Accordingly, it may be desirable to modify the thresholds to a particular patient.

In another embodiment, regardless of whether sensor 32 monitors patient motion or sensor 46 monitors one or more physiological parameters, processor 34 may compare the signal generated by sensor 32 and/or sensor 46 to one or more amplitude thresholds stored within memory 38, where each threshold crossing counts as an activity count, and the total number of activity counts indicates the patient activity level.

Based on the monitored patient activity level, processor 34 of IMD 42 determines whether patient 14 transitions from the sleep state to an awake state (54). The "awake state" is associated with an activity level that is higher than sedentary, in order to properly reflect when patient 14 physically walked or otherwise moved to another location (e.g., a bathroom) to void. As described in further detail below, in one embodiment, IMD 42 determines whether patient 14 transitioned from the sleep state to the awake state (54) by comparing the patient activity level to an awake threshold. In another embodiment, IMD 42 determines whether patient 14 transitioned from the sleep state to the awake state by monitoring a sleep metric that indicates a probability that patient 14 is asleep or awake. The sleep metric may also be used to determine whether patient 14 is sleeping or attempting to sleep.

If IMD 42 determines that patient 14 did not transition from a sleep state to an awake state, but, rather, patient 14 is still in the sleep state, IMD 42 may continue monitoring the activity level (52). If IMD 42 determines that patient 14 transitioned from a sleep state to an awake state, IMD 42 continues to monitor the activity level to determine whether patient 14 transitions back to a sleep state within a certain amount of time (56). Fluctuations between a sleep state and an awake state indicate that the patient's sleep state was interrupted. Limiting the amount of time in which patient 14 may return to the sleep state from the awake state helps to ensure that the sleep state did not end, but rather, the sleep state was interrupted.

If the patient activity level indicates the patient's sleep state was interrupted (54), IMD 42 continues to monitor the activity level to determine whether a subsequent patient activity level indicates that patient 14 returned to a sleep state (56). As described in further detail below, in one embodiment, IMD 42 determines whether patient 14 transitioned from an awake state to a sleep state (56) by comparing the patient activity level to an awake threshold. In another embodiment, IMD 42 determines whether patient 14 transitioned from the awake state to the sleep state (56) by monitoring a sleep metric that indicates a probability that patient 14 is asleep or awake.

Examples of circuits that may be used to detect transitions between a sleep state and awake state based on various physiological parameters or other indicators of activity levels are described in U.S. patent application Ser. No. 11/691,425, entitled, "COLLECTING ACTIVITY AND SLEEP QUALITY INFORMATION VIA A MEDICAL DEVICE" and filed on Mar. 26, 2007, which published on Mar. 20, 2008 as U.S. Publication No. 2008/0071150 and which is incorporated herein by reference in its entirety.

If the patient 14 transitioned back to the sleep state from the awake state, processor 34 Of IMD 42 records of awake count in memory 38 (58). The amount of time within which patient 14 may transition back to sleep state before IMD 42 records an awake count (58) may be predetermined by a clinician, and may be specific to a particular patient, or may be used for more than one patient. For example, in some embodiments, the amount of time may transition back to the sleep state prior to recording the awake count may be less than an hour or less than two hours. In general, the amount of time should be short enough to distinguish between the time between sleep events (e.g., the time between two separate nights of sleep) and the time it might take patient 14 to avoid and return to sleep state. Limiting the amount of time in which patient 14 may fall back into the sleep state prior recording an awake count helps ensure that the awake counts are associated with a single sleep event (e.g., one night of sleep verses multiple nights of sleep) generally represents the number of interruptions in the sleep state of patient 14 that are attributable to nocturia. Therefore, in one embodiment, processor 34 determines a number of nocturia events based on the determined number of interruptions in the sleep state of patient 14.

In addition to recording an awake count, in some embodiments, processor 34 may record the date and time of the awake count was generated. For example, IMD 42 may include a clock that is coupled to processor 34, which may obtain a clock signal from the clock to associate a timestamp with the awake count. Processor 34 may associate a timestamp with a detected voiding event by sending a request signal to the clock. In response to receiving the control signal, the clock may generate a signal that represents the time. Alternatively, the clock may output the signal to processor 34 substantially continuously and processor 34 can examine the signal in response to recording an awake count. The clock may also be used to activate when processor 34 beings detecting a sleep state (50) and monitoring the patient's activity level (52), which may decrease the processor's power consumption.

In some cases, after an awake count is recorded, thus indicating that a voiding event occurred, it may be unlikely that another voiding event will occur for a certain amount of time, such as thirty minutes to an hour, but the time may be more or less. Accordingly, in some embodiments, after recording an awake count (58), processor 34 may enter into a "blanking" mode, which processor 34 waits a certain prescribed amount of time before detecting another sleep state and beginning the process over to detect a nocturia event. The prescribed amount of time may be determined by a clinician or a manufacturer of IMD 42. The blanking mode may help processor 34 conserve energy, which may help extend the useful life of IMD 42. On the other hand, a blanking state may not be useful for all patients.

If patient 14 did not transition back to the sleep state, processor 34 begins detecting detects another sleep event by detecting another sleep state (50), and begins the process over for the other sleep event. The process shown in FIG. 4 may be repeated for each sleep state detected by processor 34 of IMD 42, where each sleep state is associated with a new sleep event.

In some embodiments, IMD 42 does not determine whether patient 14 transitioned between a sleep state and awake state (54, 56) or record the awake counts, but instead provides monitored activity levels to a computing device, such as clinician programmer 22 (FIG. 1) or patient programmer 24 (FIG. 1). In such embodiments, the computing device may analyze activity stored within memory 38 of IMD 42 and determine the number of times patient 14 transitioned from the sleep state to the awake state (54) and back to the sleep state (56). In this way, the computing device may record awake counts and determine the number of interruptions in the sleep state of the patient. The clinician may use the number of interruptions in the sleep state of the patient to evaluate the efficacy of therapy. Additionally, IMD 42 need not monitor the activity levels, but may instead store samples of the signals generated by sensors 32 and/or 46. In such embodiments, the computing device may determine both activity levels and the number of awake counts for each sleep state.

Figure 5:
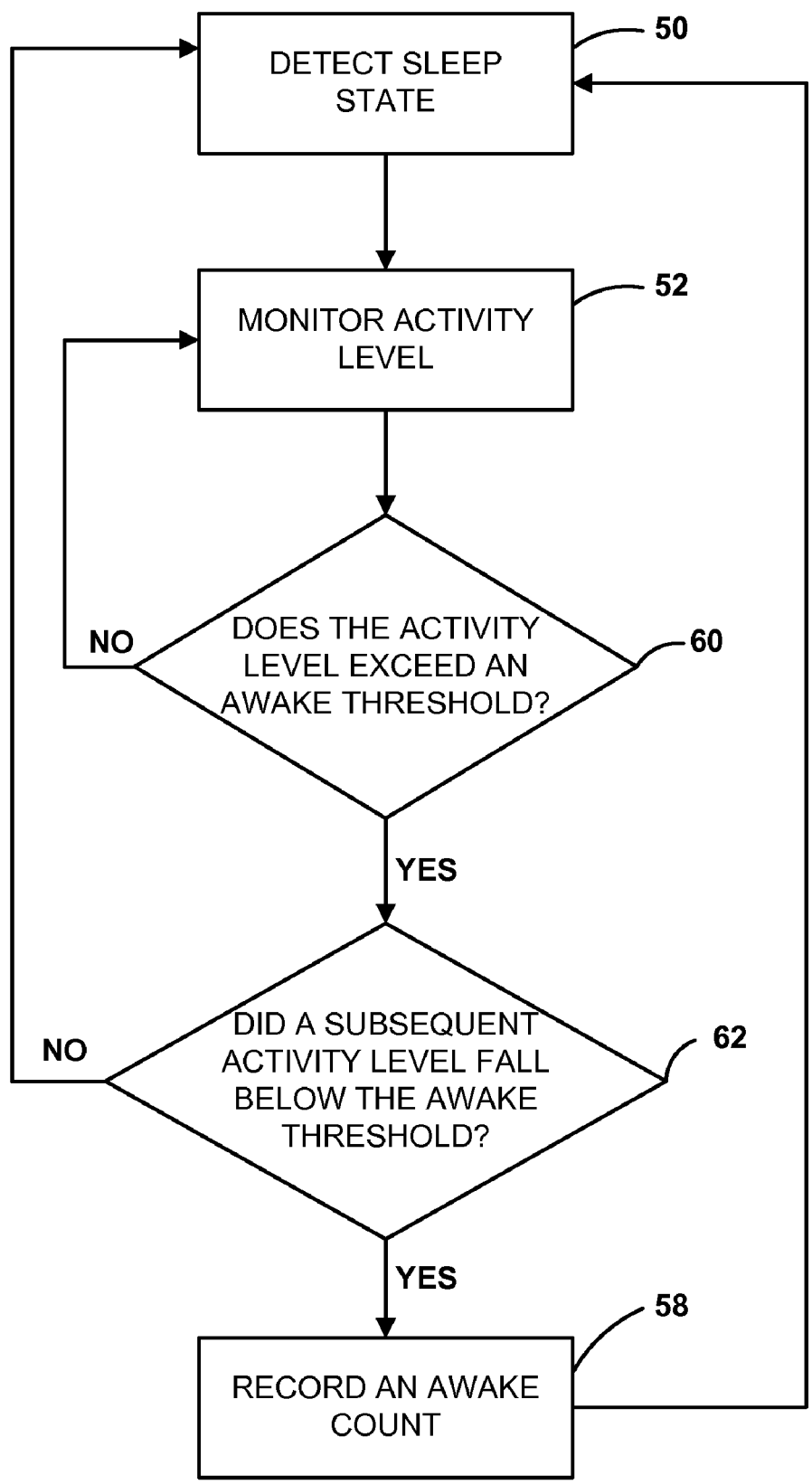
FIGS. 5 to 7 are each flow diagrams illustrating embodiments of a method of determining a number of interruptions in a sleep state of patient.

As previously described, in one embodiment, IMD 42 may determine whether patient 14 transitioned between an awake state and a sleep state (54, 56) by comparing a determined patient activity level to an awake threshold. FIG. 5 illustrates a flow diagram of one technique for determining a number of interruptions in a sleep state of patient 14, where the technique includes comparing the patient activity level to an awake threshold in order to determine whether patient 14 transitioned between an awake state and a sleep state. As with the technique shown in FIG. 4, processor 34 of IMD 42 detects a sleep state (50) and monitors a patient activity level (52). Processor 34 compares the patient activity level to an awake threshold (60), which is an activity level at or above which the patient is not only awake, but indicates the patient is active (versus sedentary). Because the relevant determination is whether the patient's sleep state is interrupted because of nocturia, the relevant awake threshold is an activity level that indicates patient 14 not only is awake, but is active, rather than sedentary. For example, the awake threshold is an activity level that indicates patient 14 is getting out of bed to void or walking to a bathroom. The activity level for patient 14 during the sleep state may differ from the activity levels of other patients, and accordingly, the awake threshold may be tailored to a particular patient. Alternatively, the awake threshold may be common to two or more patients.

If the patient activity level does not exceed the awake threshold (60), IMD 42 continues to monitor the activity level (52) until the patient activity level exceeds the awake threshold, if ever. After determining that patient 14 awoke from a sleep state, IMD 42 monitors the activity level to ensure that patient 14 returns to a sleep state (62) and that the sleep state did not end. In particular, if the patient activity level exceeds the awake threshold (60), IMD 42 continues to monitor the activity level to determine whether a subsequent patient activity level falls below the awake threshold within a certain amount of time (62). If the patient activity level exceeds the awake threshold (60), thus indicating that patient 14 awoke from the sleep state, and then falls below the threshold within a certain amount of time, thus indicating that patient 14 returned to a sleep state (62), IMD 42 records an awake count (58). The amount of time within which a subsequent activity level may fall below the awake threshold prior to recording an awake count (58) may be determined by the clinician, and may be, for example, less than twenty minutes, less than one hour or less than two hours.

In an embodiment in which IMD 42 includes sensor 32 that generates a signal indicative of patient motion, the activity thresholds may be associated with gross motor activity of the patient, e.g., walking, running or the like. Accordingly, it is highly unlikely that patient 14 is in a sleep state if the activity level exceeds the threshold associated with a motor activity such as walking. Alternatively, as described with reference to FIG. 4, sensor 32 may be used to determine a posture of patient 14.

In an embodiment in which IMD 42 utilizes physiological parameter sensor 46 to monitor an activity level of patient 14, the detected values of physiological parameters of patient 14, such as heart rate, ECG morphological features, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response may discernibly change when patient 14 falls asleep or awakes. Some of these physiological parameters may be at low values when patient 14 is asleep. Further, the variability of at least some of these parameters, such as heart rate and respiration rate, may be at a low value when the patient is asleep.

Consequently, in order to detect when patient 14 falls asleep and wakes up, processor 34 may monitor one or more of these physiological parameters, or the variability of these physiological parameters, and detect the discernable changes in their values associated with a transition between a sleep state and an awake state. In some embodiments, processor 34 may determine a mean or median value for a parameter based on values of a signal over time, and determine whether patient 14 is asleep or awake based on the mean or median value. Processor 34 may compare one or more parameter values or parameter variability values to thresholds stored in memory 38 (60, 62) to detect when patient 14 transitions from the sleep state to the awake state or vice versa. The thresholds may be absolute values of a physiological parameter, or time rate of change values for the physiological parameter, e.g., to detect sudden changes in the value of a parameter or parameter variability. In some embodiments, a threshold used by processor 34 to determine whether patient 14 is asleep may include a time component. For example, a threshold may require that a physiological parameter be above or below a threshold value for a period of time before processor 34 determines that patient is awake or asleep.

As an alternative to comparing activity levels to thresholds, the relative changes in a patient's activity level may be used to determine when the patient is in an elevated activity state that reflects an interruption in the sleep state. For example, after determining a sleep state has commence, processor 34 may monitor the activity levels for changes in the activity level, where an increase or sudden change in one or more of heart rate, heart rate variability, respiration rate, respiration rate variability, blood pressure, ECG morphological features or muscular activity indicates an increase in activity associated with a transition from the sleep state to the awake state, or vice versa. The rate or amount of change in the physiological parameter or variability may be compared to a threshold stored in memory 38.

In another embodiment, processor 34 of IMD 42 determines whether patient 14 transitioned from the awake state to the sleep state (56, FIG. 4) by monitoring a plurality of physiological parameters, and determining a value of a metric that indicates the probability that the patient 14 is asleep for each of the parameters based on a value of the physiological parameter. Because the physiological parameter varies as a function of patient activity, the metric also varies as a function of patient activity, and therefore, is one way of monitoring the patient activity level.

Figure 6:
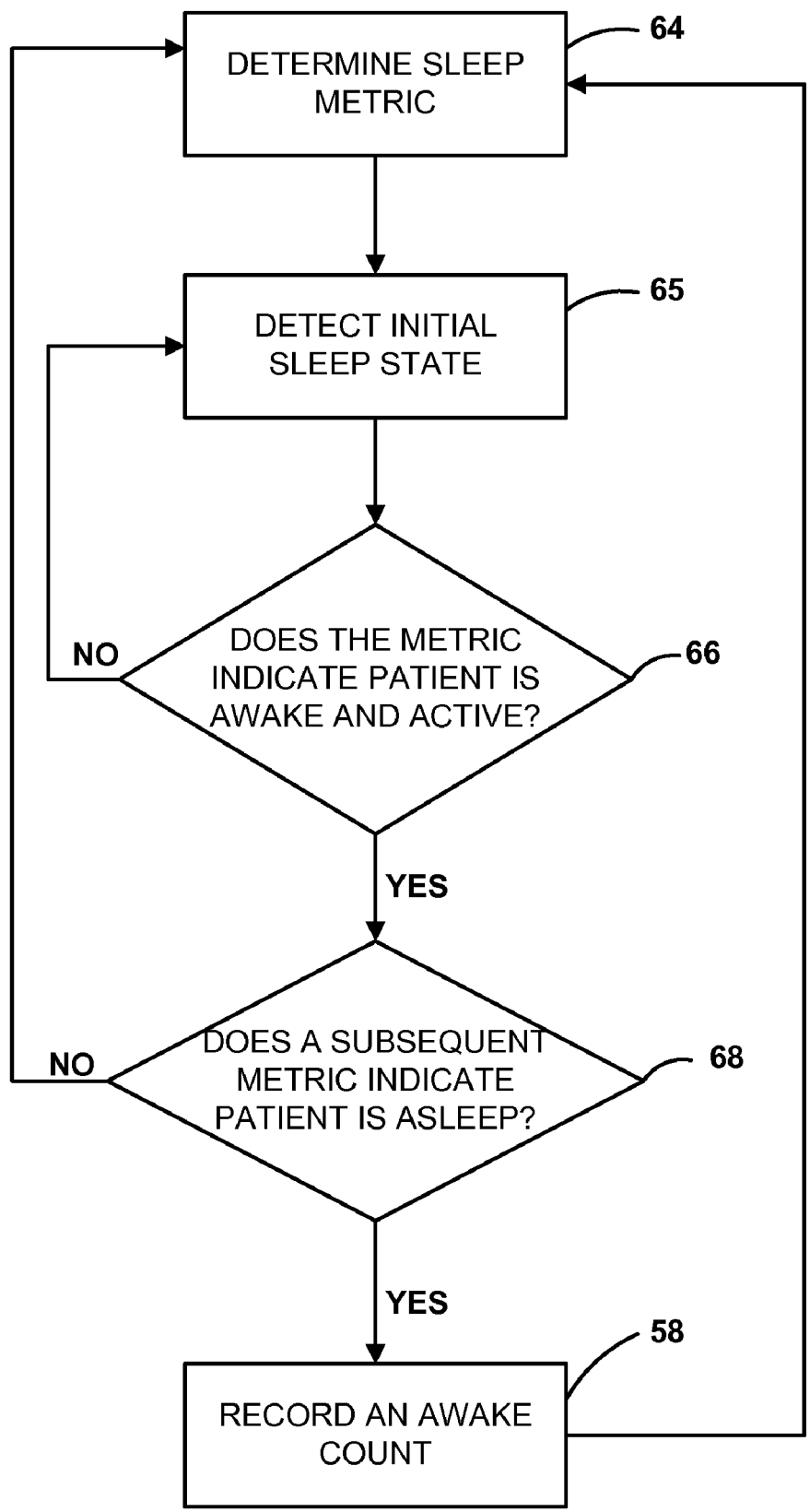

FIG. 6 is a flow diagram of a technique that determines a number of interruptions in a sleep state of patient 14 by analyzing one or more sleep metrics that indicate the probability that the patient 14 is asleep. In particular, processor 34 determines a sleep metric (64) by applying a function or look-up table to the current, mean or median value, and/or the variability of each of a plurality of physiological parameters determined based on signals from sensor 46. A sleep metric value may be a numeric value, and in some embodiments may be a probability value, e.g., a number within the range from 0 to 1, or a percentage value.

Processor 34 may average or otherwise combine the plurality of sleep metric values to provide an overall sleep metric value. In some embodiments, processor 34 may apply a weighting factor to one or more of the sleep metric values prior to combination. Use of sleep metric values to determine when a patient is asleep based on a plurality of monitored physiological parameters is described in greater detail in a commonly-assigned and copending U.S. patent application Ser. No. 11/691,405, entitled "DETECTING SLEEP TO EVALUATE THERAPY," and filed on Mar. 26, 2007, which published on Mar. 20, 2008 as U.S. Publication No. 2008/0071326 and which is incorporated herein by reference in its entirety.

Based on a determined sleep metric (64), processor 34 may detect an initial sleep state (65), such as by comparing an overall sleep metric value or a particular sleep metric value to one or more threshold values stored in memory 38 to determine when patient 14 has entered a sleep state. Processor 34 may continue monitoring the sleep metric to determine whether the metric indicates the patient is awake and active (66). Again, the relevant determination is whether the patient's sleep was interrupted by an act of getting out of bed to void. Processor 34 may compare the overall sleep metric value to one or more threshold values stored in memory 38 to determine when patient 14 is asleep or awake and active. If not, processor 34 continues to monitor the one or more physiological parameters via sensor 46 and determine sleep metric based on the sensed physiological parameters. If the sleep metric indicates the patient is awake, processor 34 determines whether a subsequent metric based on subsequently sensed physiological parameters measured within a certain amount of time from the time it is determined that patient 14 is awake indicate the patient is asleep (68). As previously described, processor 34 determines whether patient 14 returned to the sleep state within a certain amount of time in order to help ensure that any further awake counts are associated with the correct sleep event. If patient 14 returns to the sleep state, processor 34 records an awake count in memory 38. If not, processor 34 detects another sleep event by detecting another sleep state (50), and begins the process over for the other sleep event.

Figure 7:
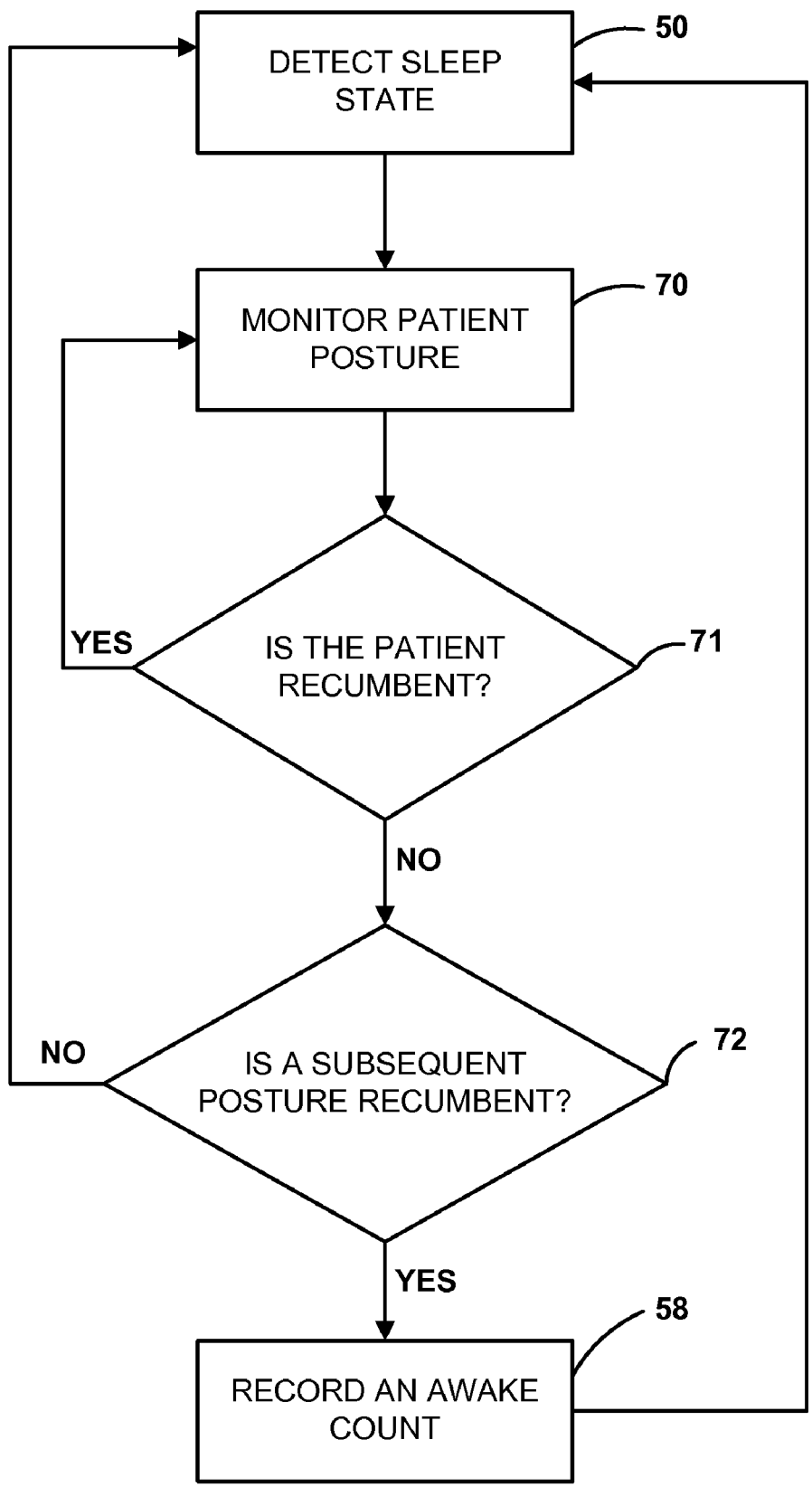

In another embodiment of the process shown in FIG. 4, processor 34 of IMD 42 determines whether patient 14 transitioned from the awake state to the sleep state (56, FIG. 4) by monitoring a posture of patient 14, where posture is one type of patient activity. FIG. 7 is a flow diagram of a technique that determines a number of interruptions in a sleep state of patient 14 by analyzing changes in posture of patient 14. After detecting the start of a sleep state (50), processor 34 may monitor the posture of patient 14. The posture of patient 14 may be determined via any of the techniques described above with respect to FIG. 4. For example, sensor 32 may comprise a multi-axis accelerometer that generates a signal indicative of the posture of patient 14.

Typically, patient 14 is recumbent when sleeping. Accordingly, a deviation from the recumbent posture may indicate that patient 14 is in an awake state and active, which indicates that patient 14 awoke to void. Thus, the process shown in FIG. 7 includes determining whether patient 14 is recumbent (70), and thus, asleep. However, if patient 14 sleeps in a posture other than recumbent, the other posture may be used as the baseline to detect a change in posture that indicates patient 14 is in an awake state. The posture data may be used in addition to a physiological parameter, such as muscle activity, to determine whether the patient's posture not only changed, but whether patient 14 got up to void. Embodiments in which processor 34 monitors both the posture and activity level of patient 14 may provide a good indication of circumstances surrounding a patient activity level. That is, monitoring both posture and activity data may provide a robust technique for determining whether patient 14 is in a sleep state or an awake state. In some cases, patient activity level alone may not clearly indicate whether patient 14 is transitioning between and awake and sleep state because patient 14 may be moving around while trying to fall asleep. Combining the activity level with a patient posture may indicate whether the patient is in the sleep state or awake state. For example, a relatively high level of activity (e.g., crossing a threshold indicating that patient 14 is "active") while patient 14 is recumbent may indicate patient 14 is in the sleep state, but is having trouble falling asleep. On the other hand, a relatively high level activity while patient 14 is standing or otherwise upright may indicate patient 14 is in an awake state for the purposes of recording an awake count. As another example, a relatively low level of activity may indicate patient 14 is asleep, and detecting a recumbent posture may validate the sleep state determination.

Returning now to FIG. 7, if patient 14 is recumbent, and thus still in the sleep state, processor 34 may continue monitoring patient posture (70) until a change in posture is detected, if at all. If processor 34 determines that patient 14 is no longer recumbent (71), and, thus, patient 14 is awake, processor 34 may continue monitoring the posture to detect a change in posture back to the recumbent posture (72). If processor 34 detects a subsequent recumbent posture within a certain amount of time, such as less than one or two hours, processor 34 records an awake count in memory 38 of IMD 42.

Figure 8A:
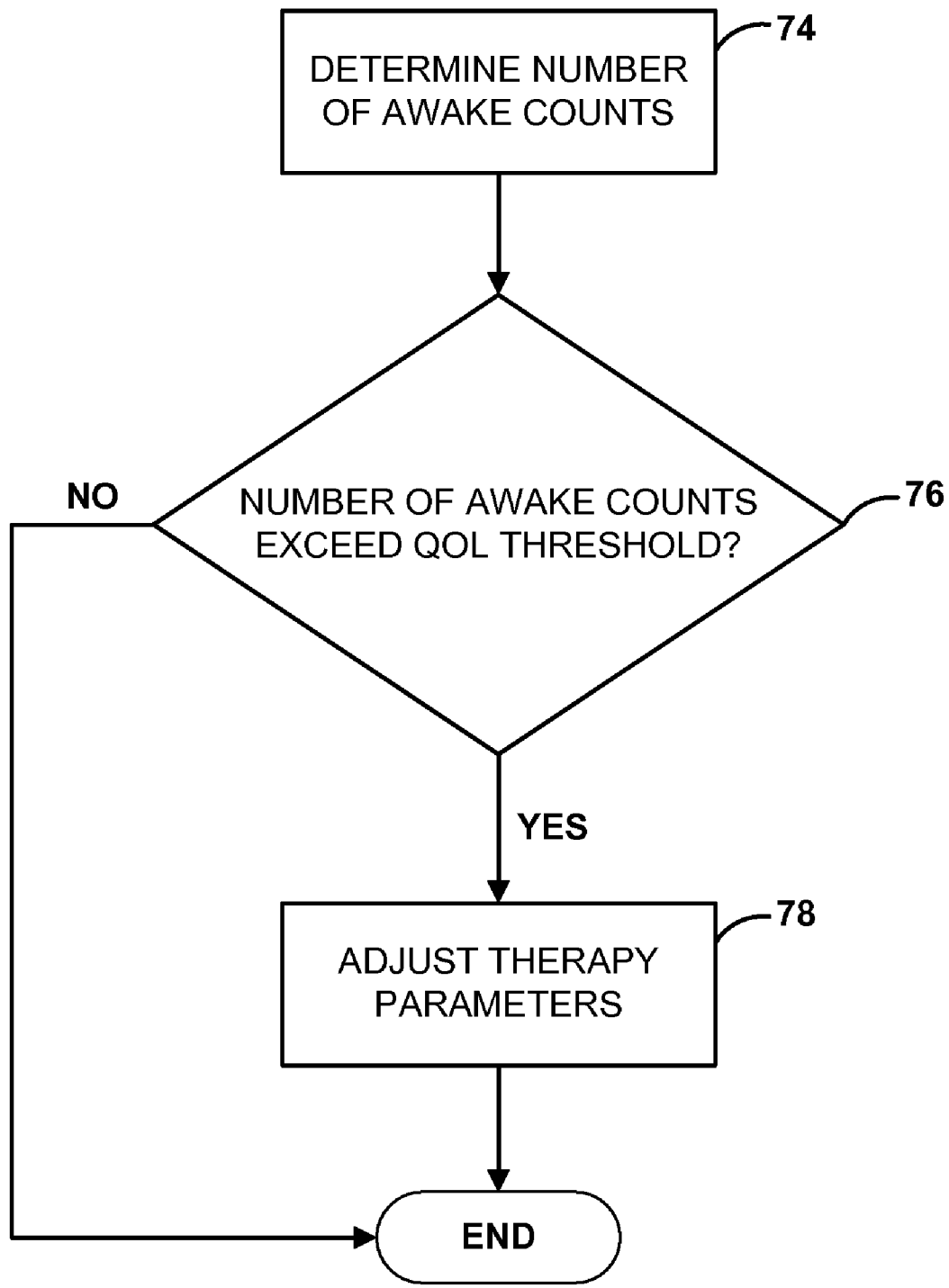
FIGS. 8A and 8B are flow diagrams illustrating techniques for adjusting stimulation parameters based on a number of awake counts determined using, for example, any of the methods shown in FIGS. 4-6.

FIG. 8A is a flow diagram illustrating a technique for adjusting therapy parameters based on the number of awake counts determined using any of the processes shown in FIGS. 4-6. After processor 34 of IMD 42 or another computing device determines a number of awake counts (74) for a sleep event, which indicates the number of interruptions in the sleep state of patient 14 during the sleep event, a clinician may compare the number of awake counts to a quality of life (QOL) threshold (76). If the number of awake counts for more than one sleep event (e.g., each night of sleep for a week or month) are determined, the clinician may average the awake counts and compare the average awake count to the QOL threshold, or may compare the number of awake counts for each sleep event to the QOL threshold.

The QOL threshold indicates the number of interruptions during a sleep state (i.e., the number of sleep counts) due to a need to void at or above which the quality of life of patient 14 is adversely affected. The QOL threshold may be determined by the clinician or the patient. For example, patient 14 may decide that it is unacceptable and negatively impacts the quality of life to get up more than two times during a sleep state to void. Thus, in that case, the QOL threshold would be two. As another example, the clinician may decide to reevaluate a patient's therapy parameter set only if patient 14 averages about three awake counts or more. Thus, in that case, the QOL threshold would be three. Any QOL threshold may be used in the process shown in FIG. 8A.

If the number of awake counts stored in memory 38 of IMD 42 or a memory of another device, such as clinician programmer 22 or patient programmer 24 (FIG. 1), exceeds or is equal to the QOL threshold, the clinician may adjust the therapy parameters (78). For example, the clinician may modify the voltage or current amplitude, pulse width or pulse frequency of the stimulation of electrical stimulation therapy delivered by therapy module 30 of IMD 42 in order to better control bladder 12 and limit the number of interruptions in sleep attributable to nocturia. Stimulation parameter adaptation logic that may be implemented by processor 34 or one of programmers 22, 24 is discussed in commonly-assigned U.S. patent application Ser. No. 11/117,058, entitled, "IMPLANTABLE MEDICAL DEVICE PROVIDING ADAPTIVE NEUROSTIMULATION THERAPY FOR INCONTINENCE," and filed on Apr. 28, 2005, which issued on Aug. 25, 2009 as U.S. Pat. No. 7,580,752 and which is incorporated herein by reference in its entirety.

If the number of awake counts does not exceed the QOL threshold, the clinician may either end the process. The process shown in FIG. 8A may be repeated if more awake counts are determined. If no therapy parameter set is implemented for patient 14, the clinician may choose to implant IMD 42 or use an external device for chronic therapy when the awake count exceeds the QOL threshold. In other words, a clinician may decide whether to provide a therapy based on a comparison of a number of awake counts to a QOL threshold.

In another embodiment, processor 34 of IMD 42, rather than a clinician, may automatically adjust the therapy parameters (78) upon determining that the QOL threshold is exceeded (76), whether the QOL threshold is exceeded at the beginning, middle or end of the sleep state. In this way, activity data from sensor 32 and/or sensor 46 may be used to define a closed loop system that provides feedback to processor 34 to automatically adjust therapy parameters (78). An advantage to adjusting therapy parameters as soon as the number of awake counts exceeds the QOL threshold is that any adverse impact on the patient's sleep state due to nocturia is almost immediately identified and addressed. If the therapy parameters are adjusted at the beginning or midway through the sleep state, the number of further interruptions throughout the remainder of the patient's sleep state may be limited.

Figure 8B:
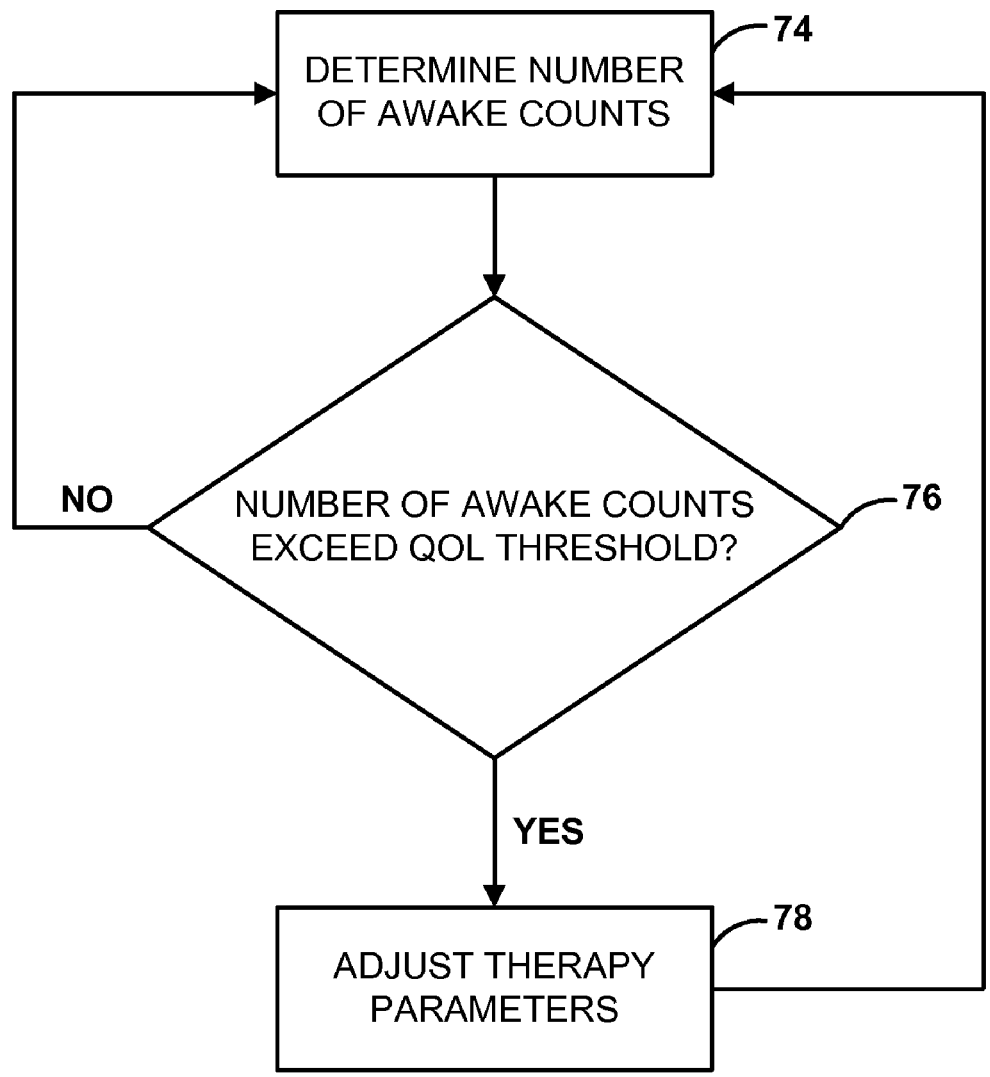

The number of awake counts may be compared to the QOL threshold (76) after a trial period in which patient 14 is sent home to gather awake counts for a period of time, such as a few days to a month or more. Alternatively, if processor 34 of IMD 42 compares the number of awake counts to the QOL threshold (76), processor 34 may continuously compare the number of awake counts during a sleep state to the QOL threshold. A flow diagram illustrating this process is shown in FIG. 8B. The flow diagram in FIG. 8B is substantially similar to the diagram shown in FIG. 8A, except that the process includes determining the number of awake counts (74) until the number exceeds the QOL threshold. In addition, the process shown in FIG. 8B continues to determine the number of awake counts (74) after the therapy parameters are adjusted (78). The closed loop cycle for adjusting therapy parameters shown in FIG. 8B may be employed may processor 34 of IMD 42 or another device for automatic adjustment of therapy parameters for a chronic therapy delivery parameter set.

Figure 9:
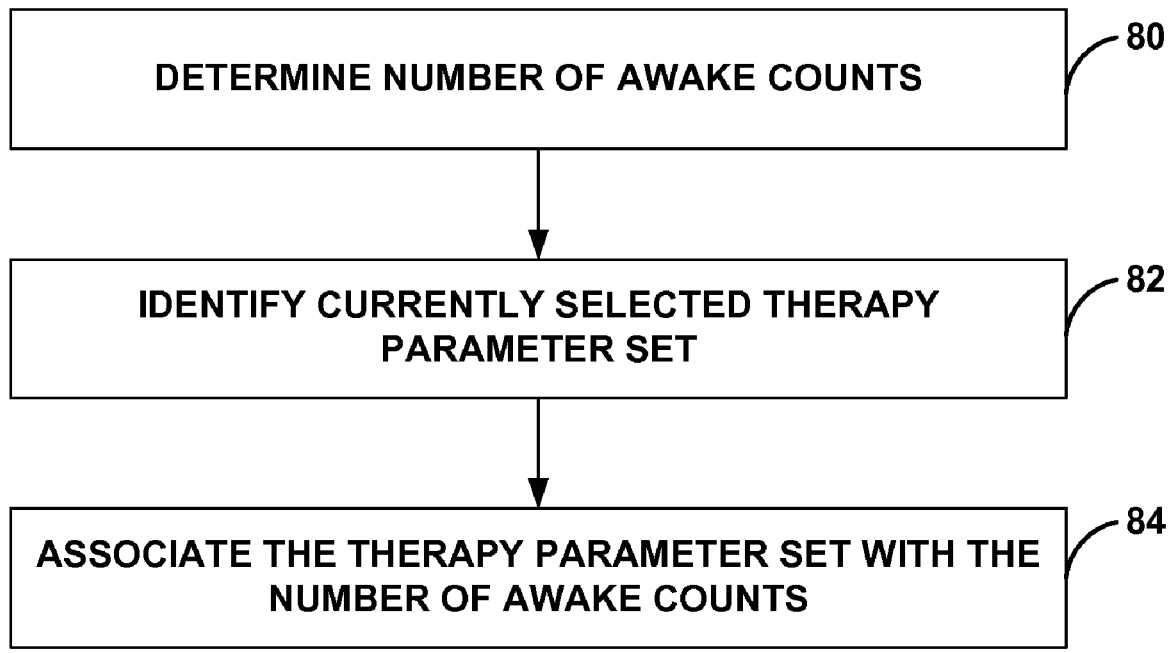
FIG. 9 is a flow diagram illustrating an embodiment of a method for associating the number of awake counts with one or more therapy parameter sets that may be employed by a medical device.

FIG. 9 is a flow diagram illustrating an embodiment of a method for associating the number of awake counts with one or more therapy parameter sets that may be employed by IMD 42. IMD 42 determines a total number of awake counts for a sleep event of patient 14 or an average or mean awake count for multiple sleep events of patient 14 according to any of the techniques described above (80). IMD 42 also identifies the current therapy parameter set, i.e., the therapy parameter set that was employed by IMD 42 to control delivery of therapy when the number of awake counts was determined (82), and associates the number of awake counts with the current therapy parameter set (84). If a number of awake counts is already associated with the current therapy parameter set, IMD 42 may update number of awake counts or average the number of awake counts associated with the particular therapy parameter set.

In other embodiments, a computing device, such as clinician programmer 22 or patient programmer 24 (FIG. 1) may associate a number of awake counts with the therapy parameter set employed by IMD 42 when the number of awake counts was determined.

Associating a number of awake counts or other awake count information with a therapy parameter set may be useful for evaluating the efficacy of the therapy parameter set and comparing the effectiveness of a plurality of therapy parameter sets. "Awake count information" generally refers to a total number of awake counts that were determined while the therapy parameter set was employed, the frequency of the awake counts averaged over the duration of the sleep state or some other period of time, the time each awake count associated with the therapy parameter set was recorded or other similar information.

Figure 10:
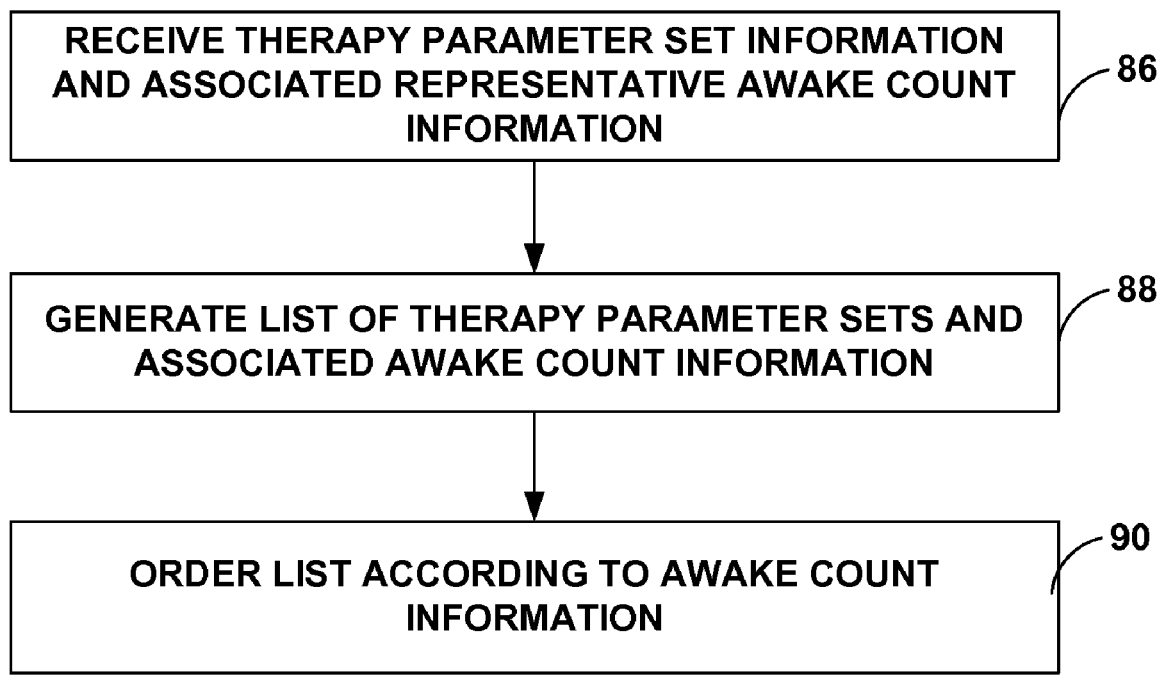
FIG. 10 is a flow diagram illustrating an example method for displaying a list of therapy parameter sets and associated awake count information that may be employed by a clinician programmer.

FIG. 10 is a flow diagram illustrating an example method for displaying a list of therapy parameter sets and associated awake count information that may be employed by clinician programmer 22 (FIG. 1). Clinician programmer 22 receives information identifying the plurality of therapy parameter sets stored in memory 38 of IMD 42 and awake count information associated with each of the parameter sets (86). Clinician programmer 22 generates a list of the therapy parameter sets and associated awake count information (88), and orders the list according to the awake count information (90). For example, clinician programmer 22 may order the list of parameter sets by the total number of awake counts, where the therapy parameter set associated with the fewest number of awake counts is presented first. The clinician may review and scroll through the list via input keys 23A and display 23B of clinician programmer 22. Based on the list, the clinician may choose to eliminate one or more therapy parameter sets as being ineffective to control the nocturia, or the clinician may select one or more therapy parameter sets to employ during a sleep state of the patient because the fewest number of awake counts are associated with those parameter sets. Thus, associating a number of awake counts with a therapy parameter set may be useful for evaluating therapy parameter sets during a trial period, prior to programming the parameter sets within IMD 42 for delivery of stimulation therapy on a chronic basis.

In the above embodiments, sensors that are configured to generate a signal that is indicative of patient activity levels are shown to be integrated with IMD 42 that also delivers therapy to patient 14 to control nocturia. In other embodiments, the sensors may be external and/or separate from IMD 42. External activity sensors may be useful for diagnosing nocturia prior to implanting IMD 42 to treat the nocturia, such as during a trial period in which the severity of the patient's nocturia is evaluated. External activity sensors are also useful for other situations in which it is desirable to automatically generate a log recording the number of times patient 14 awakes during a sleep state to void. Automatically generating the log may be more convenient to patient 14, and may help minimize error in the patient's account of the number of sleep interruptions.

Figure 11:
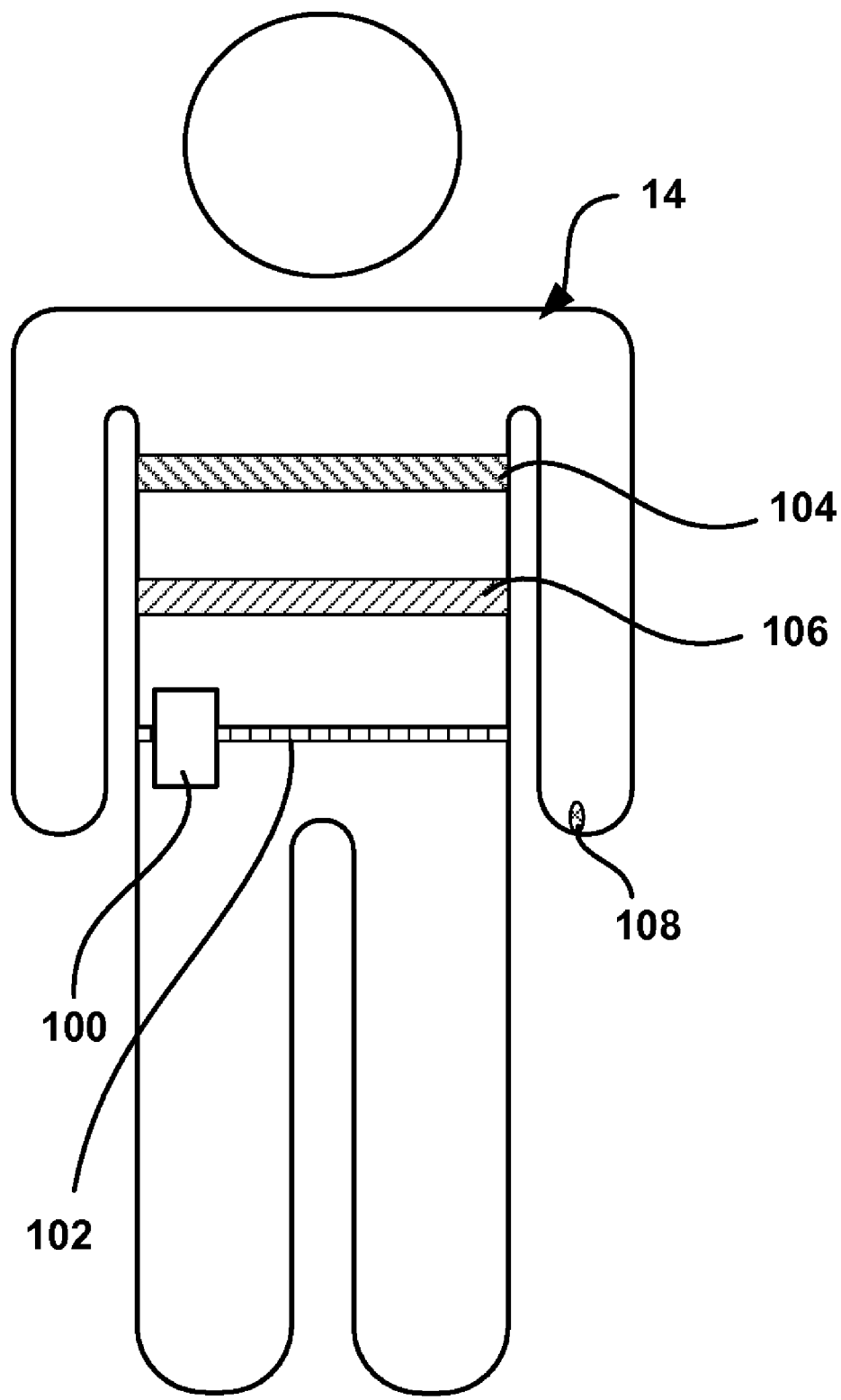
FIG. 11 is a schematic diagram of an external activity sensing device that may be used to determine a patient activity level.

FIG. 11 is a schematic diagram illustrating external activity sensing device 100 that may be used to monitor an activity level of patient 14 to determine a number of awake counts during a sleep state. Activity sensing device 100 is an external device that may be attached to patient 14 via a belt 102. Alternatively, activity sensing device 100 may be attached to patient 14 by any other suitable technique, such as a clip that attaches to the patient's clothing, or activity sensing device 100 may be worn on a necklace that is worn around the patient's neck or a watch on the patient's wrist. Activity sensing device 100 may include a sensor that generates a signal indicative of patient motion, such as accelerometer or a piezoelectric crystal. If activity sensing device 100 includes a sensor that senses relative motion, such as an accelerometer, it may be desirable to attach sensing device 100 to a torso of patient 14 in order to gather the most relevant activity data.

In addition to or instead of a motion sensor, sensing device 100 may include or be coupled to a sensor that generates a signal that indicates a physiological parameter that varies as a function of patient activity to determine an activity level of patient 14. As described above, the physiological parameter may be heart rate, respiratory rate, ECG morphology, respiration rate, respiratory volume, core temperature, a muscular activity level, subcutaneous temperature or electromyographic activity of patient 14. For example, in some embodiments, patient 14 may wear an ECG belt 104 that incorporates a plurality of electrodes for sensing the electrical activity of the heart of patient 14. The heart rate and, in some embodiments, ECG morphology of patient 14 may monitored based on the signal provided by ECG belt 104. Examples of suitable ECG belts for sensing the heart rate of patient 14 are the "M" and "F" heart rate monitor models commercially available from Polar Electro. In some embodiments, instead of ECG belt 104, patient 14 may wear a plurality of ECG electrodes (not shown in FIG. 11) attached, e.g., via adhesive patches, at various locations on the chest of patient 14, as is known in the art. An ECG signal derived from the signals sensed by such an array of electrodes may enable both heart rate and ECG morphology monitoring, as is known in the art.

A respiration belt 106 that outputs a signal that varies as a function of respiration of the patient may also be worn by patient 14 to monitor activity to determine whether patient 14 awakes during a sleep state to void. Respiration belt 106 may be a plethysmograpy belt, and the signal output by respiration belt 106 may vary as a function of the changes is the thoracic or abdominal circumference of patient 14 that accompany breathing by patient 14. An example of a suitable respiration belt is the TSD201 Respiratory Effort Transducer commercially available from Biopac Systems, Inc. Alternatively, respiration belt 106 may incorporate or be replaced by a plurality of electrodes that direct an electrical signal through the thorax of patient 14, and circuitry to sense the impedance of the thorax, which varies as a function of respiration of patient 14, based on the signal. In some embodiments, the ECG and respiration belts 104, 106 may be a common belt worn by patient 14.

Patient 14 may also wear transducer 108 that outputs a signal as a function of the oxygen saturation of the blood of patient 14. Transducer 108 may be an infrared transducer. Transducer 108 may be located on one of the fingers or earlobes of patient 14. Each of the types of sensors 100, 104, 106, and 108 described above may be used alone or in combination with each other.

Figure 12:
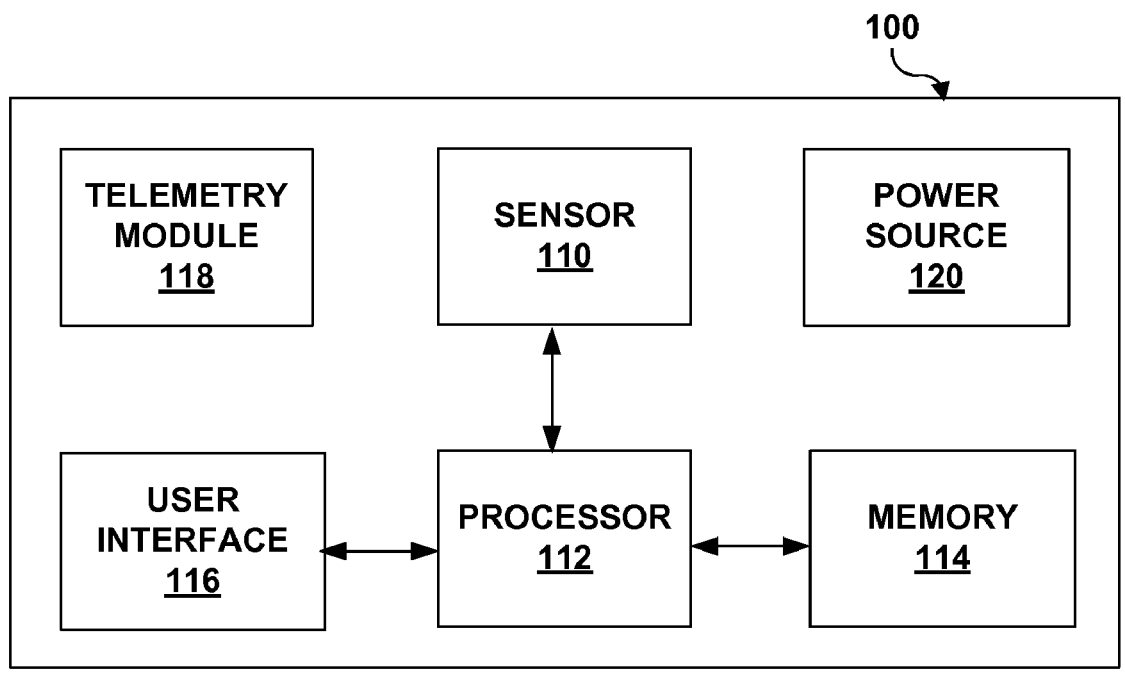
FIG. 12 is a schematic block diagram of an activity sensing device, which includes a sensor, processor, memory, power source, and user interface.

FIG. 12 is a schematic block diagram of activity sensing device 100, which includes sensor 110, processor 112, memory 114, user interface 116, telemetry module 118, and power source 120. Activity sensing device 100 is configured to generate a signal indicative of a patient activity level. Sensor 110 may be any sensor such as an accelerometer, a bonded piezoelectric crystal, a mercury switch, or a gyro, or any other sensor that transforms mechanical, chemical or electrical conditions into electrical signals representative of an activity level of patient 14. The electrical signals may be amplified, filtered, and otherwise processed as appropriate by circuitry known in the art, which may be provided as part of sensor 110 or processor 112. In some embodiments, the signals may be converted to digital values and processed by processor 112 before being saved to memory 114 or uploaded to another device (e.g., a clinician computing device).

In some cases, sensor 110 may measure a physiological parameter of patient 14 that varies as a function of patient activity. However, because sensor 110 is worn externally to patient 14, some physiological parameter measurements may not be as accurate as measurements taken via sensor 46, which is implanted within patient 14.

Processor 112 may be similar to processor 34 of IMD 16, 42. Processor 112 is electrically coupled to sensor 110 and receives a signal from sensor 110 in order to monitor the signal and determine a patient activity level based on the signal using any of the techniques described above with respect to processor 34. Alternatively, processor 112 does not determine an activity level, but merely stores the signals from sensor 110 in memory 114 for later retrieval and analysis by a clinician. The clinician may, for example, upload the data from memory 114 onto clinician programmer 22 (FIG. 1), which may then determine the activity levels based on the stored signals.

The data from sensor 110 and/or patient activity levels determined by processor 112 may be stored in memory 114 of activity sensing device 100. Memory 114 is similar to memory 38 of IMD 16, 42. The data from memory 114 may be uploaded to another device via telemetry module 118, which may be controlled by processor 112. Telemetry module 118 may communicate with another device using any of a variety of local wireless communication techniques, such as RF communication according to the 802.11 or Bluetooth specification sets, infrared communication, e.g., according to the IrDA standard, or other standard or proprietary telemetry protocols.

Sensor 110 and processor 112 may be coupled to power source 120. Power source 120 may take the form of a rechargeable or non-rechargeable battery. In the case of a rechargeable battery, power source 120 may include an inductive power interface for transfer of recharge power. In other embodiments, activity sensors could also be integrated into a programming device, which may be "worn" in some fashion by a patient during a sleep event.

In the illustrated embodiments of FIG. 1-3, IMDs 16, 42 take the form of implantable electrical stimulators that deliver electrical stimulation therapy to patient 14. However, the invention is not limited to implementation via implantable electrical stimulators. For example, in some embodiments of the invention, an implantable pump or implantable cardiac rhythm management device, such as a pacemaker may collect patient activity information. Such devices may deliver therapy according to therapy parameter sets in the manner described above. For example, an implantable pump may deliver therapy according to a set of therapy parameters such as flow rate, concentration or duty cycle. Further, the invention is not limited to implementation via an IMD. In other words, any implantable or external medical device or computing device may collect activity count information according to the invention.

Patients with fecal incontinence may also be afflicted with the need or urge to void during a sleep event, thereby interrupting the sleep state of the patient. The systems and methods described herein are also useful for determining a number of times a patient awakes during a sleep state to void when the patient is afflicted with fecal incontinence, and if applicable, adjusting therapy parameters based on the awake count information, selecting a therapy based on the awake count information, and so forth. Fecal incontinence may also be controlled via electrical stimulation therapy or drug delivery therapy. As an example, electrical stimulation may be delivered to the nerves that control the anal sphincters, nerves that sense stool in the rectum, or muscles of the rectum, such as internal or external sphincters, and a lead carrying one or more electrodes may be implanted proximate to the relevant structures within the patient.

Various embodiments of the invention have been described. These and other embodiments are within the scope of the following claims.

The invention claimed is:

1. A system comprising:
an implantable activity sensor that generates a signal that varies as a function of activity of a patient; and
at least one processor that is configured to receive the signal from the activity sensor, detect a sleep state of the patient, determine a first number of interruptions in the sleep state of the patient based on the signal, and determine a second number of sleep event voiding events based on the number of interruptions in the sleep state of the patient.

2. The system of claim 1, wherein the at least one processor is configured to adjust a therapy parameter to treat sleep event voiding based on the number of interruptions in the sleep state.

3. The system of claim 2, further comprising a memory, wherein the at least one processor is configured to compare the number of interruptions in the sleep state to a quality of life threshold stored in the memory and adjust the therapy parameter if the number of interruptions exceeds the quality of life threshold.

4. The system of claim 2, wherein the therapy parameter comprises at least one of voltage or current amplitude of electrical stimulation, pulse width of electrical stimulation, pulse frequency of electrical stimulation, a drug dosage, or a frequency of a delivery of a drug.

5. The system of claim 2, wherein the at least one processor is configured to adjust a therapy parameter by at least selecting a therapy parameter set to treat sleep event voiding based on the number of interruptions in the sleep state.

6. The system of claim 1, wherein the at least one processor is configured to select a therapy parameter set to treat sleep event voiding based on the number of interruptions in the sleep state.

7. The system of claim 1, wherein the at least one processor is configured to detect the sleep state of the patient by receiving an indication from the patient that the patient is attempting to sleep.

8. The system of claim 1, wherein the at least one processor is configured to detect the sleep state of the patient based on the signal from the activity sensor.

9. The system of claim 1, further comprising a memory, wherein the at least one processor is configured to determine an activity level of the patient based on the signal, determine the number of interruptions in the sleep state of the patient by comparing the activity level to an activity level threshold stored in the memory, and determine when the activity level exceeds the activity level threshold.

10. The system of claim 9, wherein the at least one processor is configured to generate an awake count when the activity level exceeds the activity level threshold and a subsequent activity level falls below the activity level threshold within a predetermined range of time, wherein each awake count represents an interruption in the sleep state.

11. The system of claim 9, wherein the implantable activity sensor senses a physiological parameter to generate the signal.

12. The system of claim 11, wherein the signal comprises a first signal, the system further comprising a posture sensor that generates a second signal that indicates a posture of the patient, wherein the at least one processor is configured to determine the first number of interruptions in the sleep state of the patient based on the first and second signals.

13. The system of claim 9, wherein the implantable activity sensor comprises at least one of an accelerometer, a bonded piezoelectric crystal, a mercury switch or a gyro.

14. The system of claim 9, wherein the signal comprises a first signal, the system further comprising a posture sensor that generates a second signal that indicates a posture of the patient, wherein the at least one processor is configured to determine the first number of interruptions in the sleep state of the patient based on the first and second signals.

15. The system of claim 1, further comprising a memory, wherein implantable activity sensor senses a physiological parameter to generate the signal, wherein the at least one processor is configured to determine the number of interruptions in the sleep state of the patient by determining a value of at least one metric that indicates a probability that the patient is asleep or awake based on the signal, and compare the metric to a threshold stored in the memory.

16. The system of claim 1, wherein the signal is indicative of a physiological parameter of the patient, the physiological parameter comprising at least one of posture, heart rate, respiration rate, respiratory volume, core temperature, blood pressure, blood oxygen saturation, partial pressure of oxygen within blood, partial pressure of oxygen within cerebrospinal fluid, muscular activity, arterial blood flow, and galvanic skin response.

17. The system of claim 1, wherein the implantable activity sensor comprises at least one of an accelerometer, a bonded piezoelectric crystal, a mercury switch or a gyro.

18. The system of claim 1, further comprising a therapy module configured to deliver a therapy to the patient via a therapy parameter set, wherein the at least one processor is configured to associate the number of interruptions in the sleep state with the therapy parameter set.

19. The system of claim 18, wherein the sleep state is a first sleep state, the number of interruptions is a first number of interruptions, and the therapy parameter set is a first therapy parameter set, wherein the at least one processor is configured to:
    detect a second sleep state of the patient;
    determine a second number of interruptions in the second sleep state of the patient based on the signal;
    associate the second number of interruptions in the second sleep state with a second therapy parameter set.

20. The system of claim 19, further comprising an external programming device including a display that receives information identifying the first and second therapy parameter sets and the first and second number of interruptions in the sleep state associated with the respective first and second therapy parameter sets from the implantable medical device, and presents a list of the first and second therapy parameter sets and the associated first and second number of interruptions in the sleep state to a user via the display.

21. The system of claim 19, wherein the at least one processor is configured to select one of the first or second therapy parameter sets for delivering therapy to the patient based on the respective first and second number of interruptions.

22. The system of claim 19, wherein the at least one processor is configured to rank the first and second therapy parameter sets according to the respective first and second number of interruptions.

23. A system comprising:
    an activity sensor that generates a signal that varies as a function of activity of a patient;
    a therapy delivery module configured to deliver a therapy to the patient to control sleep event voiding; and
    a processor configured to receive the signal from the activity sensor, detect a sleep state of the patient, determine a number of interruptions in the sleep state of the patient based on the signal, determine a number of sleep event voiding events based on the number of interruptions in the sleep state of the patient, and adjust a parameter of the therapy based on the number of sleep event voiding events.

24. The system of claim 23, wherein the activity sensor is implantable.

25. The system of claim 23, wherein the therapy parameter comprises at least one of voltage or current amplitude, pulse width or pulse frequency of electrical stimulation, or a drug dosage or a frequency of a delivery of a drug.

26. The system of claim 23, wherein the processor is configured to compare the number of interruptions in the sleep state to a quality of life threshold, and adjust the therapy parameter if the number of interruptions exceeds the quality of life threshold.

27. The system of claim 23, wherein the sleep state is a first sleep state, the number of interruptions is a first number of interruptions, and the parameter is part of a first therapy parameter set with which the therapy module delivers the therapy to the patient during the first sleep state, wherein the at least one processor is configured to:
    detect a second sleep state of the patient;
    determine a second number of interruptions in the second sleep state of the patient based on the signal;
    associate the second number of interruptions in the second sleep state with a second therapy parameter set with which the therapy module delivers the therapy to the patient during the second sleep state; and
    select one of the first or second therapy parameter sets for delivering therapy to the patient based on the respective first and second number of interruptions.

* * * * *